US007339049B1

(12) United States Patent
Chee et al.

(10) Patent No.: US 7,339,049 B1
(45) Date of Patent: Mar. 4, 2008

(54) POLYMORPHISMS IN HUMAN MITOCHONDRIAL DNA

(75) Inventors: Mark Chee, Palo Alto, CA (US); Anthony Berno, San Jose, CA (US); Robert Yang, San Ramon, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 08/856,376

(22) Filed: May 14, 1997

Related U.S. Application Data

(60) Provisional application No. 60/024,206, filed on Aug. 20, 1996, provisional application No. 60/017,203, filed on May 16, 1996.

(51) Int. Cl.
*C07H 21/04* (2006.01)
*C07H 21/02* (2006.01)
*C12Q 1/68* (2006.01)
*C12N 1/20* (2006.01)
*C12N 15/00* (2006.01)
*C12N 5/02* (2006.01)

(52) U.S. Cl. ............... 536/24.1; 435/6; 435/252.3; 435/320.1; 435/325; 536/23.1

(58) Field of Classification Search ............ 435/6; 536/23.1, 24.1, 24.3–24.33
See application file for complete search history.

(56) References Cited

U.S. PATENT DOCUMENTS

| | | | |
|---|---|---|---|
| 5,206,137 A | 4/1993 | Ip et al. ............... | 435/6 |
| 5,292,639 A | 3/1994 | Beitz et al. ............ | 435/6 |
| 5,468,610 A | 11/1995 | Polymeropoulos et al. | 435/6 |
| 5,494,794 A * | 2/1996 | Wallace ............... | 435/6 |
| 5,565,523 A * | 10/1996 | Parker et al. .......... | 435/6 |
| 5,760,205 A * | 6/1998 | Parker et al. .......... | 536/23.5 |
| 5,840,493 A * | 11/1998 | Davis et al. ........... | 435/6 |

OTHER PUBLICATIONS

Anderson et al., Nature, vol. 290, pp. 457-465, 1981.*
1990 Sigma Catalog [Publ. by Sigma Chemical Company, P.O. Box 14508, St. Louis, Missouri, USA.] p. 776, 1990.*
Stoneking et al., American Journal of Human Genetics, vol. 48, pp. 370-380, 1991.*
Aquadro et al., Genetics, vol. 103, pp. 287-312, 1983.*
Chee, Mark et al., "Accessing Genetic Information With High-density DNA Arrays", *Science*, (Oct. 25, 1996) vol. 274, pp. 610-614.
Curriden, Mark, "A New Evidence Tool", *ABA Journal* (Nov. 1996) p. 18.
Davis, Robert E. et al., "Mutations In Mitochondrial Cytochrome *c* Oxidase Genes Segregate With Late-Onset Alzheimer Disease", *Proc. Natl. Acad. Sci. USA*, (Apr. 1997) vol. 94, pp. 4526-4531.
Fan, Jian-Bing et al., "Screening the Human Genome for Single-nucleotide Polymorphisms by Hybridization to High-density Oligonucleotide Arrays", Mutation Detection '97, 4th International Workshop (May 29-Jun. 2, 1997, Brno, Czech Rebublic) 1 page.

Greenberg, Barry D. et al., "Intraspecific Nucleotide Sequence Variability Surrounding the Origin of Replication in Human Mitochondrial DNA", (1983) *Gene*, vol. 21, pp. 33-49.
Kwok, Pui-Yan et al., "Increasing the Information content of STS-Based Genome Maps: Identifying Polymorphisms in Mapped STSs", *Genomics*, (1996) vol. 31, Article No. 0019, pp. 123-126.
Wallace, Douglas C., "Diseases of the Mitochondrial DNA", *Annu. Rev. Biochem.* (1992) vol. 61, pp. 1175-1212.
Ginther et al., "Identifying individuals by sequencing mitochondrial DNA from teeth." Nature Genetics, 2:135 (Oct. 1992).
Greenberg et al., "Intraspecific nucleotide sequence variability surrounding the origin of replication in human mitochondrial DNA," Gene 21(1-2):33 (1983).
Howell et al., "Mitochondrial gene segregation in humans: is the bottleneck always narrow?" Human Genetics, 90:117 (1992).
Howell et al., "When does bilateral optic atrophy become Leber hereditary optic atrophy?" American Journal of Human Genetics, 53:959 (1993).
Hutchin et al., "A molecular basis for human hypersensitivity to aminoglycoside antibiotics," NAR 21(18):4174 (1993).
Ikebe et al., "Point mutations of mitochondrial genome in PArkinson's disease," Molecular Brain Research 28(2):281 (1995).
Isenberg and Moore, "Mitochondrial DNA Analysis at the FBI Laboratory," Forensic Science Communications, vol. 1, No. 2 (Jul. 1999).
Johns and Neufeld, "Pitfalls in the molecular genetic diagnosis of Leber hereditary optic neuropathy (LHON)," American Journal of Human Genetics, 53 (4):916 (1993).
Marzuki et al., "Normal variants of human mitochondrial DNA and translation products: building a reference data base," Human Genetics, 88 (2):139 (1991).
Mehta, et al., "A new genetic polymorphism in the 16S ribosomal RNA gene of human mitochondrial DNA," Annals of Human Genetics, 53 (Pt. 4):303 (1989).
Moraes, et al., "Two novel pathogenic mitochondrial DNA mutations affecting organelle number and protein synthesis. Is the tRNA Leu(UUR) gene an etiologic hot spot?" J. of Clinical Investigation, 92(6):2906 (1993).
Ozawa et al., "Distinct clustering of point mutations in mitochondrial DNA amoung patients with mitochondrial encephalomyopathies and with Parkinson's disease," BBRC, 176 (2):938 (1991).
Ozawa et al., "Patients with idiopathic cardiomyopathy belong to the same mitochondrial gene family of Parkinson's disease and mitochondrial encephalomyopathy," BBRC 177(1):518 (1991).

(Continued)

*Primary Examiner*—Shubo (Joe) Zhou
(74) *Attorney, Agent, or Firm*—Sandra E. Wells

(57) ABSTRACT

The invention provides novel human mitochondrial polymorphisms, and probes and primers for detecting the same. Detection of such polymorphisms is useful in a variety of fields such as forensic analysis, epidemiology and preventive medicine.

65 Claims, 3 Drawing Sheets

OTHER PUBLICATIONS

Petruzzella et al., "Is a point mutation in the mitochondrial ND2 gene associated with Alzheimer's disease?" BBRC 186:491 (1992).

Prezant et al., "Mitochondrial ribosomal RNA mutation associated with both antibiotic-induced and non-syndromic deafness," Nature Genetics, 4 (3):289-294(1993).

Reid et al., "Complete mtDNA sequence of a patient in a maternal pedigree with sensorineural deafness," Human Molecular Genetics, 3(8):1435 (1994).

Ruvolo et al., Mitochondrial COII sequences and modern huiman origins, Molecular Biology and Evolution, 10:1115 (1993).

Seneca et al., "Importance of sequence analysis in the NARP syndrome," J. Inherited Metabolic Disorders, 18 (1):97 (1995).

Tanaka and Ozawa, "Strand asymmetry in human mitochondrial DNA mutations," Genomics, 22(2):327 (1994).

Graven et al., "Evolutionary Correlation between Control Region Sequence and Restriction Polymorphismns in the Mitochondrial Genome of a Large Senegalese Mandenka Sample," Mol. Biol. Evol., 12(2):334-345.

Lipshutz et al., "Using Oligonucleotide Probe Arrays To Access Genetic Diversity," BioTechniques, 19(3):442-447 (1995).

Petros et al., "mtDNA mutations increase tumorigenicity in prostate cancer," PNAS, 102(3):719-824 (2005).

* cited by examiner

Figure 1

A
```
5' ..TGAACTGTATCCGACAT..
3'     tgacat ggctgtag
       tgacatCggctgtag
       tgacatGggctgtag
       tgacatTggctgtag
3'      gacataAgctgtaga
        gacataCgctgtaga
        gacata gctgtaga
        gacataTgctgtaga
```

B
```
5' ..TGAACTGTACCCGACAT..
3'     tgacatAggctgtag
       tgacatCggctgtag
       tgacat ggctgtag
       tgacatTggctgtag
3'      gacataAgctgtaga
        gacataCgctgtaga
        gacata gctgtaga
        gacataTgctgtaga
```

C
5' TGAACTGTATCCGACAT

5' TGAACTGTACCCGACAT

16,493

SEQUENCE LISTING

<160> NUMBER OF SEQ ID NOS: 30

<210> SEQ ID NO 1
<211> LENGTH: 41
<212> TYPE: DNA
<213> ORGANISM: Artificial Sequence
<220> FEATURE:
<223> OTHER INFORMATION: Primer for human mitochondrial DNA

<400> SEQUENCE: 1
ctcggaatta accctcacta aaggaaacct ttttccaagg a        41

<210> SEQ ID NO 2
<211> LENGTH: 42
<212> TYPE: DNA
<213> ORGANISM: Artificial Sequence
<220> FEATURE:
<223> OTHER INFORMATION: Primer for human mitochondrial DNA

<400> SEQUENCE: 2
taatacgact cactataggg agaggctagg accaaaccta tt        42

<210> SEQ ID NO 3
<211> LENGTH: 15
<212> TYPE: DNA
<213> ORGANISM: Artificial Sequence
<220> FEATURE:
<223> OTHER INFORMATION: Probe for human mitochondrial DNA

<400> SEQUENCE: 3
gatgtcggat acagt        15

<210> SEQ ID NO 4
<211> LENGTH: 15
<212> TYPE: DNA
<213> ORGANISM: Artificial Sequence
<220> FEATURE:
<223> OTHER INFORMATION: Probe for human mitochondrial DNA

<400> SEQUENCE: 4
gatgtcggct acagt                                                         15

<210> SEQ ID NO 5
<211> LENGTH: 15
<212> TYPE: DNA
<213> ORGANISM: Artificial Sequence
<220> FEATURE:
<223> OTHER INFORMATION: Primer for human mitochondrial DNA

<400> SEQUENCE: 5
gatgtcgggt acagt                                                         15

<210> SEQ ID NO 6
<211> LENGTH: 15
<212> TYPE: DNA
<213> ORGANISM: Artificial Sequence
<220> FEATURE:
<223> OTHER INFORMATION: Primer for human mitochondrial DNA

<400> SEQUENCE: 6
gatgtcggtt acagt                                                         15

<210> SEQ ID NO 7
<211> LENGTH: 20
<212> TYPE: DNA
<213> ORGANISM: Artificial Sequence
<220> FEATURE:
<223> OTHER INFORMATION: Synthetic Control Oligonucleotide

<400> SEQUENCE: 7
ctgaacggta gcatcttgac                                                    20

<210> SEQ ID NO 8
<211> LENGTH: 40
<212> TYPE: DNA
<213> ORGANISM: Artificial Sequence
<220> FEATURE:
<223> OTHER INFORMATION: Primer for human mitochondrial DNA

<400> SEQUENCE: 8
aattaaccct cactaaaggg attctcgcac ggactacaac                              40

<210> SEQ ID NO 9
<211> LENGTH: 45
<212> TYPE: DNA
<213> ORGANISM: Artificial Sequence
<220> FEATURE:
<223> OTHER INFORMATION: Primer for human mitochondrial DNA

<400> SEQUENCE: 9
aattaaccct cactaaaggg atgaaacttc ggctcactcc ttggc                        45

<210> SEQ ID NO 10
<211> LENGTH: 47
<212> TYPE: DNA
<213> ORGANISM: Artificial Sequence
<220> FEATURE:
<223> OTHER INFORMATION: Primer for human mitochondrial DNA -continued

<400> SEQUENCE: 10
taatacgact cactataggg atttcatcat gcggagatgt tggatgg          47

<210> SEQ ID NO 11
<211> LENGTH: 20
<212> TYPE: DNA
<213> ORGANISM: Artificial Sequence
<220> FEATURE:
<223> OTHER INFORMATION: Synthetic Control Oligonucleotide

<400> SEQUENCE: 11
ctgaacggta gcatcttgac                                         20

<210> SEQ ID NO 12
<211> LENGTH: 17
<212> TYPE: DNA
<213> ORGANISM: Artificial Sequence
<220> FEATURE:
<223> OTHER INFORMATION: Synthetic Control Oligonucleotide

<400> SEQUENCE: 12
tgaactgtat ccgacat                                            17

<210> SEQ ID NO 13
<211> LENGTH: 14
<212> TYPE: DNA
<213> ORGANISM: Artificial Sequence
<220> FEATURE:
<223> OTHER INFORMATION: Probe for human mitochondrial DNA

<400> SEQUENCE: 13
gatgtcggta cagt                                               14

<210> SEQ ID NO 14
<211> LENGTH: 15
<212> TYPE: DNA
<213> ORGANISM: Artificial Sequence
<220> FEATURE:
<223> OTHER INFORMATION: Probe for human mitochondrial DNA

<400> SEQUENCE: 14
gatgtcggct acagt                                              15

<210> SEQ ID NO 15
<211> LENGTH: 15
<212> TYPE: DNA
<213> ORGANISM: Artificial Sequence
<220> FEATURE:
<223> OTHER INFORMATION: Probe for human mitochondrial DNA

<400> SEQUENCE: 15
gatgtcgggt acagt                                              15

<210> SEQ ID NO 16
<211> LENGTH: 15
<212> TYPE: DNA
<213> ORGANISM: Artificial Sequence
<220> FEATURE:
<223> OTHER INFORMATION: Probe for human mitochondrial DNA

<400> SEQUENCE: 16
gatgtcggtt acagt                                              15

<210> SEQ ID NO 17

```
<211> LENGTH: 15
<212> TYPE: DNA
<213> ORGANISM: Artificial Sequence
<220> FEATURE:
<223> OTHER INFORMATION: Probe for human mitochondrial DNA

<400> SEQUENCE: 17
agatgtcgaa tacag                                                     15

<210> SEQ ID NO 18
<211> LENGTH: 15
<212> TYPE: DNA
<213> ORGANISM: Artificial Sequence
<220> FEATURE:
<223> OTHER INFORMATION: Probe for human mitochondrial DNA

<400> SEQUENCE: 18
agatgtcgca tacag                                                     15

<210> SEQ ID NO 19
<211> LENGTH: 14
<212> TYPE: DNA
<213> ORGANISM: Artificial Sequence
<220> FEATURE:
<223> OTHER INFORMATION: Probe for human mitochondrial DNA

<400> SEQUENCE: 19
agatgtcgat acag                                                      14

<210> SEQ ID NO 20
<211> LENGTH: 15
<212> TYPE: DNA
<213> ORGANISM: Artificial Sequence
<220> FEATURE:
<223> OTHER INFORMATION: Probe for human mitochondrial DNA

<400> SEQUENCE: 20
agatgtcgta tacag                                                     15

<210> SEQ ID NO 21
<211> LENGTH: 17
<212> TYPE: DNA
<213> ORGANISM: Artificial Sequence
<220> FEATURE:
<223> OTHER INFORMATION: Probe for human mitochondrial DNA

<400> SEQUENCE: 21
tgaactgtac ccgacat                                                   17

<210> SEQ ID NO 22
<211> LENGTH: 15
<212> TYPE: DNA
<213> ORGANISM: Artificial Sequence
<220> FEATURE:
<223> OTHER INFORMATION: Probe for human mitochondrial DNA

<400> SEQUENCE: 22
gatgtcggat acagt                                                     15

<210> SEQ ID NO 23
<211> LENGTH: 15
<212> TYPE: DNA
<213> ORGANISM: Artificial Sequence
<220> FEATURE:
<223> OTHER INFORMATION: Probe for human mitochondrial DNA

<400> SEQUENCE: 23
```

```
gatgtcggct acagt                                              15

<210> SEQ ID NO 24
<211> LENGTH: 14
<212> TYPE: DNA
<213> ORGANISM: Artificial Sequence
<220> FEATURE:
<223> OTHER INFORMATION: Probe for human mitochondrial DNA

<400> SEQUENCE: 24
gatgtcggta cagt                                               14

<210> SEQ ID NO 25
<211> LENGTH: 15
<212> TYPE: DNA
<213> ORGANISM: Artificial Sequence
<220> FEATURE:
<223> OTHER INFORMATION: Probe for human mitochondrial DNA

<400> SEQUENCE: 25
gatgtcggtt acagt                                              15

<210> SEQ ID NO 26
<211> LENGTH: 15
<212> TYPE: DNA
<213> ORGANISM: Artificial Sequence
<220> FEATURE:
<223> OTHER INFORMATION: Probe for human mitochondrial DNA

<400> SEQUENCE: 26
agatgtcgaa tacag                                              15

<210> SEQ ID NO 27
<211> LENGTH: 15
<212> TYPE: DNA
<213> ORGANISM: Artificial Sequence
<220> FEATURE:
<223> OTHER INFORMATION: Probe for human mitochondrial DNA

<400> SEQUENCE: 27
agatgtcgca tacag                                              15

<210> SEQ ID NO 28
<211> LENGTH: 14
<212> TYPE: DNA
<213> ORGANISM: Artificial Sequence
<220> FEATURE:
<223> OTHER INFORMATION: Probe for human mitochondrial DNA

<400> SEQUENCE: 28
agatgtcgat acag                                               14

<210> SEQ ID NO 29
<211> LENGTH: 15
<212> TYPE: DNA
<213> ORGANISM: Artificial Sequence
<220> FEATURE:
<223> OTHER INFORMATION: Probe for human mitochondrial DNA

<400> SEQUENCE: 29
agatgtcgta tacag                                              15

<210> SEQ ID NO 30
<211> LENGTH: 16569
<212> TYPE: DNA
```

<213> ORGANISM: Homo sapiens

<400> SEQUENCE: 30

```
gatcacaggt ctatcaccct attaaccact cacgggagct ctccatgcat ttggtatttt      60
cgtctggggg gtatgcacgc gatagcattg cgagacgctg gagccggagc accctatgtc     120
gcagtatctg tctttgattc ctgcctcatc ctattattta tcgcacctac gttcaatatt     180
acaggcgaac atacttacta aagtgtgtta attaattaat gcttgtagga cataataata     240
acaattgaat gtctgcacag ccactttcca cacagacatc ataacaaaaa atttccacca     300
aaccccccct cccccgcttc tggccacagc acttaaacac atctctgcca accccaaaa     360
acaaagaacc ctaacaccag cctaaccaga tttcaaattt tatcttttgg cggtatgcac     420
ttttaacagt cacccccaa ctaacacatt attttcccct cccactccca tactactaat     480
ctcatcaata caaccccgc ccatcctacc cagcacacac accgctgc taacccata       540
ccccgaacca accaaacccc aaagacaccc cccacagttt atgtagctta cctcctcaaa     600
gcaatacact gaaaatgttt agacgggctc acatcacccc ataaacaaat aggtttggtc     660
ctagcctttc tattagctct tagtaagatt acacatgcaa gcatcccgt tccagtgagt     720
tcaccctcta aatcaccacg atcaaaaggg acaagcatca agcacgcagc aatgcagctc     780
aaaacgctta gcctagccac acccccacgg gaaacagcag tgattaacct ttagcaataa     840
acgaaagttt aactaagcta tactaacccc agggttggtc aatttcgtgc cagccaccgc     900
ggtcacacga ttaacccaag tcaatagaag ccggcgtaaa gagtgtttta gatcacccc      960
tccccaataa agctaaaact cacctgagtt gtaaaaaact ccagttgaca caaaatagac    1020
tacgaaagtg gctttaacat atctgaacac acaatagcta agacccaaac tgggattaga    1080
taccccacta tgcttagccc taaacctcaa cagttaaatc aacaaaactg ctcgccagaa    1140
cactacgagc cacagcttaa aactcaaagg acctggcggt gcttcatatc cctctagagg    1200
agcctgttct gtaatcgata aaccccgatc aacctcacca cctcttgctc agcctatata    1260
ccgccatctt cagcaaaccc tgatgaaggc tacaaagtaa cgcaagtac ccacgtaaag    1320
acgttaggtc aaggtgtagc ccatgaggtg gcaagaaatg ggctacattt tctacccag    1380
aaaactacga tagcccttat gaaacttaag ggtcgaaggt ggatttagca gtaaactaag    1440
agtagagtgc ttagttgaac agggccctga agcgcgtaca caccgccgt cacctcctc     1500
aagtatactt caaggacat ttaactaaaa ccctacgca tttatataga ggagacaagt    1560
cgtaacatgg taagtgtact ggaaagtgca cttggacgaa ccagagtgta gcttaacaca    1620
aagcacccaa cttacactta ggagatttca acttaacttg accgctctga gctaaaccta    1680
gccccaaacc cactccacct tactaccaga caaccttagc caaaccattt acccaaataa    1740
agtataggcg atagaaattg aaacctggcg caatagatat agtaccgcaa gggaaagatg    1800
aaaaattata accaagcata atatagcaag gactaacccc tataccttct gcataatgaa    1860
ttaactagaa ataactttgc aaggagagcc aaagctaaga ccccgaaac cagacgagct    1920
acctaagaac agctaaaaga gcacacccgt ctatgtagca aaatagtggg aagatttata    1980
ggtagaggcg acaaacctac cgagcctggt gatagctggt tgtccaagat agaatcttag    2040
ttcaactta aatttgccca cagaaccctc taaatcccct tgtaaattta actgttagtc    2100
caaagaggaa cagctctttg gacactagga aaaaccttg tagagagagt aaaaaattta    2160
acacccatag taggcctaaa agcagccacc aattaagaaa gcgttcaagc tcaacaccca    2220
ctacctaaaa aatcccaaac atataactga actcctcaca cccaattgga ccaatctatc    2280
```

-continued

```
accctataga agaactaatg ttagtataag taacatgaaa acattctcct ccgcataagc    2340
ctgcgtcaga ttaaaacact gaactgacaa ttaacagccc aatatctaca atcaaccaac    2400
aagtcattat taccctcact gtcaacccaa acaggcatg ctcataagga aaggttaaaa     2460
aaagtaaaag gaactcggca atcttaccc cgcctgttta ccaaaaacat cacctctagc     2520
atcaccagta ttagaggcac cgcctgccca gtgacacatg tttaacggcc gcggtaccct    2580
aaccgtgcaa aggtagcata atcacttgtt ccttaaatag ggacctgtat gaatggctcc    2640
acgagggttc agctgtctct tacttttaac cagtgaaatt gacctgcccg tgaagaggcg    2700
ggcataacac agcaagacga gaagacccta tggagcttta atttattaat gcaaacagta    2760
cctaacaaac ccacaggtcc taaactacca aacctgcatt aaaaatttcg gttgggcga    2820 cctcggagca gaacccaacc tccgagcagt acatgctaag acttcaccag tcaaagcgaa    2880
ctactatact caattgatcc aataacttga ccaacggaac aagttaccct agggataaca    2940
gcgcaatcct attctagagt ccatatcaac aatagggttt acgacctcga tgttggatca    3000
ggacatcccg atggtgcagc cgctattaaa ggttcgtttg ttcaacgatt aaagtcctac    3060
gtgatctgag ttcagaccgg agtaatccag gtcggtttct atctaccttc aaattcctcc    3120
ctgtacgaaa ggacaagaga ataaggcct acttcacaaa gcgccttccc ccgtaaatga     3180
tatcatctca acttagtatt atacccacac ccacccaaga acagggtttg ttaagatggc    3240
agagcccggt aatcgcataa aacttaaaac tttacagtca gaggttcaat tcctcttctt    3300
aacaacatac ccatggccaa cctcctactc ctcattgtac ccattctaat cgcaatggca    3360
ttcctaatgc ttaccgaacg aaaaattcta ggctatatac aactacgcaa aggccccaac    3420
gttgtaggcc cctacgggct actacaaccc ttcgctgacg ccataaaact cttcaccaaa    3480
gagcccctaa aacccgccac atctaccatc accctctaca tcaccgcccc gaccttagct    3540
ctcaccatcg ctcttctact atgaaccccc ctccccatac ccaacccct ggtcaacctc     3600 aacctaggcc tcctatttat tctagccacc tctagcctag ccgtttactc aatcctctga    3660
tcagggtgag catcaaactc aaactacgcc ctgatcggcg cactgcgagc agtagcccaa    3720
acaatctcat atgaagtcac cctagccatc attctactat caacattact aataagtggc    3780
tcctttaacc tctccaccct tatcacaaca caagaacacc tctgattact cctgccatca    3840
tgacccttgg ccataatatg atttatctcc acactagcag agaccaaccg aaccccttc     3900 gaccttgccg aaggggagtc cgaactagtc tcaggcttca acatcgaata cgccgcaggc    3960
cccttcgccc tattcttcat agccgaatac acaaacatta ttataataaa caccctcacc    4020
actacaatct tcctaggaac aacatatgac gcactctccc ctgaactcta cacaacatat    4080
tttgtcacca agaccctact tctaacctcc ctgttcttat gaattcgaac agcataccc    4140 cgattccgct acgaccaact catacacctc ctatgaaaaa acttcctacc actcacccta    4200
gcattactta tatgatatgt ctccataccc attacaatct ccagcattcc cctcaaacc    4260 taagaaatat gtctgataaa agagttactt tgatagagta aataatagga gcttaaaccc    4320
ccttatttct aggactatga aatcgaacc catccctgag aatccaaaat tctccgtgcc     4380
acctatcaca ccccatccta agtaaggtc agctaaataa gctatcgggc ccatacccg     4440 aaaatgttgg ttataccctt cccgtactaa ttaatcccct ggcccaaccc gtcatctact    4500
ctaccatctt tgcaggcaca ctcatcacag cgctaagctc gcactgattt tttacctgag    4560
taggcctaga aataaacatg ctagctttta ttccagttct aaccaaaaaa ataaaccctc    4620
```

-continued

```
gttccacaga agctgccatc aagtatttcc tcacgcaagc aaccgcatcc ataatccttc    4680
taatagctat cctcttcaac aatatactct ccggacaatg aaccataacc aatactacca    4740
atcaatactc atcattaata atcataatag ctatagcaat aaaactagga atagcccct     4800 ttcacttctg agtcccagag gttacccaag gcaccctct gacatccggc ctgcttcttc     4860
tcacatgaca aaaactagcc cccatctcaa tcatatacca aatctctccc tcactaaacg    4920
taagccttct cctcactctc tcaatcttat ccatcatagc aggcagttga ggtggattaa    4980
accaaaccca gctacgcaaa atcttagcat actcctcaat tacccacata ggatgaataa    5040
tagcagttct accgtacaac cctaacataa ccattcttaa tttaactatt tatattatcc    5100
taactactac cgcattccta ctactcaact aaaactccag caccacgacc ctactactat    5160
ctcgcacctg aaacaagcta acatgactaa caccctaat tccatccacc ctcctctccc    5220
taggaggcct gccccgcta accggctttt tgcccaaatg ggccattatc gaagaattca    5280
caaaaaacaa tagcctcatc atccccacca tcatagccac catcaccctc cttaacctct    5340
acttctacct acgcctaatc tactccacct caatcacact actccccata tctaacaacg    5400
taaaaataaa atgacagttt gaacatacaa aacccacccc attcctcccc cactcatcg    5460 cccttaccac gctactccta cctatctccc cttttatact aataatcctta tagaaattta   5520 ggttaaatac agaccaagag ccttcaaagc cctcagtaag ttgcaatact taatttctgt    5580
aacagctaag gactgcaaaa ccccactctg catcaactga acgcaaatca gccactttaa    5640
ttaagctaag cccttactag accaatggga cttaaaccca caaacactta gttaacagct    5700 aagcaccta atcaactggc ttcaatctac ttctcccgcc gccgggaaaa aaggcgggag     5760
aagccccggc aggtttgaag ctgcttcttc gaatttgcaa ttcaatatga aaatcacctc    5820
ggagctggta aaaagaggcc taaccctgt cttagattt acagtccaat gcttcactca     5880
gccattttac ctcaccccca ctgatgttcg ccgaccgttg actattctct acaaaccaca    5940
aagacattgg aacactatac ctattattcg gcgcatgagc tggagtccta ggcacagctc    6000
taagcctcct tattcgagcc gagctgggcc agccaggcaa ccttctaggt aacgaccaca    6060
tctacaacgt tatcgtcaca gcccatgcat ttgtaataat cttcttcata gtaatacccca   6120 tcataatcgg aggctttggc aactgactag ttcccctaat aatcggtgcc cccgatatgg    6180
cgtttccccg cataaacaac ataagcttct gactcttacc tccctctctc ctactcctgc    6240
tcgcatctgc tatagtggag gccggagcag gaacaggttg aacagtctac cctcccttag    6300
cagggaacta ctcccaccct ggagcctccg tagacctaac catcttctcc ttacacctag    6360
caggtgtctc ctctatctta ggggccatca atttcatcac aacaattatc aatataaaaac   6420 cccctgccat aacccaatac caaacgcccc tcttcgtctg atccgtccta atcacagcag    6480
tcctacttct cctatctctc ccagtcctag ctgctggcat cactatacta ctaacagacc    6540
gcaacctcaa caccaccttc ttcgaccccg ccggaggagg agaccccatt ctataccaac    6600
acctattctg attttttcggt caccctgaag tttatattct tatcctacca ggcttcggaa    6660
taatctccca tattgtaact tactactccg gaaaaaaaga accatttgga tacataggta    6720
tggtctgagc tatgatatca attggcttcc tagggtttat cgtgtgagca caccatatat    6780
ttacagtagg aatagacgta gacacacgag catatttcac ctccgctacc ataatcatcg    6840
ctatccccac cggcgtcaaa gtatttagct gactcgccac actccacgga agcaatatga    6900
aatgatctgc tgcagtgctc tgagccctag gattcatctt tcttttcacc gtaggtggcc    6960
tgactggcat tgtattagca aactcatcac tagacatcgt actacacgac acgtactacg    7020
```

```
ttgtagccca cttccactat gtcctatcaa taggagctgt atttgccatc ataggaggct   7080
tcattcactg atttccccta ttctcaggct acaccctaga ccaaacctac gccaaaatcc   7140
atttcactat catattcatc ggcgtaaatc taactttctt cccacaacac tttctcggcc   7200
tatccggaat gccccgacgt tactcggact accccgatgc ataccacca tgaaacatcc   7260 tatcatctgt aggctcattc atttctctaa cagcagtaat attaataatt ttcatgattt   7320
gagaagcctt cgcttcgaag cgaaaagtcc taatagtaga agaaccctcc ataaacctgg   7380
agtgactata tggatgcccc ccaccctacc acacattcga agaacccgta tacataaaat   7440
ctagacaaaa aaggaaggaa tcgaaccccc caaagctggt ttcaagccaa ccccatggcc   7500
tccatgactt tttcaaaaag gtattagaaa aaccatttca taactttgtc aaagttaaat   7560
tataggctaa atcctatata tcttaatggc acatgcagcg caagtaggtc tacaagacgc   7620
tacttcccct atcatagaag agcttatcac ctttcatgat cacgccctca taatcatttt   7680
ccttatctgc ttcctagtcc tgtatgccct tttcctaaca ctcacaacaa aactaactaa   7740
tactaacatc tcagacgctc aggaaataga accgtctga actatcctgc ccgccatcat   7800
cctagtcctc atcgccctcc catccctacg catcctttac ataacagacg aggtcaacga   7860
tccctcccct accatcaaat caattggcca ccaatggtac tgaacctacg agtacaccga   7920
ctacggcgga ctaatcttca actcctacat acttcccca ttattcctag aaccaggcga   7980
cctgcgactc cttgacgttg acaatcgagt agtactcccg attgaagccc ccattcgtat   8040
aataattaca tcacaagacg tcttgcactc atgagctgtc cccacattag cttaaaaac   8100 agatgcaatt cccggacgtc taaaccaaac cactttcacc gctacacgac cggggtata   8160 ctacggtcaa tgctctgaaa tctgtggagc aaaccacagt ttcatgccca tcgtcctaga   8220
attaattccc ctaaaaatct ttgaaatagg gcccgtattt accctatagc acccctcta   8280 ccccctctag agcccactgt aaagctaact tagcattaac cttttaagtt aaagattaag   8340
agaaccaaca cctctttaca gtgaaatgcc ccaactaaat actaccgtat ggcccaccat   8400 aattacccc atactcctta cactattcct catcacccaa ctaaaatat taaacacaaa   8460 ctaccaccta cctccctcac caaagcccat aaaaataaaa aattataaca aaccctgaga   8520
accaaaatga cgaaaatct gttcgcttca ttcattgccc ccacaatcct aggcctaccc   8580
gccgcagtac tgatcattct atttccccct ctattgatcc ccacctccaa atatctcatc   8640
aacaaccgac taatcaccac ccaacaatga ctaatcaaac taacctcaaa acaaatgata   8700
accatacaca acactaaagg acgaacctga tctcttatac tagtatcctt aatcattttt   8760
attgccacaa ctaacctcct cggactcctg cctcactcat ttacaccaac cacccaacta   8820
tctataaacc tagccatggc catcccctta tgagcgggca cagtgattat aggctttcgc   8880
tctaagatta aaaatgccct agcccacttc ttaccacaag gcacacctac accccttatc   8940
cccatactag ttattatcga aaccatcagc ctactcattc aaccaatagc cctggccgta   9000
cgcctaaccg ctaacattac tgcaggccac ctactcatgc acctaattgg aagcgccacc   9060
ctagcaatat caaccattaa ccttccctct acacttatca tcttcacaat tctaattcta   9120
ctgactatcc tagaaatcgc tgtcgcctta atccaagcct acgttttcac acttctagta   9180
agcctctacc tgcacgacaa cacataatga cccaccaatc acatgcctat catatagtaa   9240
aacccagccc atgaccccta acaggggccc tctcagccct cctaatgacc tccggcctag   9300
ccatgtgatt tcacttccac tccataacgc tcctcatact aggcctacta accaacacac   9360
```

-continued

```
taaccatata ccaatgatgg cgcgatgtaa cacgagaaag cacataccaa ggccaccaca   9420
caccacctgt ccaaaaaggc cttcgatacg ggataatcct atttattacc tcagaagttt   9480
tttcttcgc aggattttc tgagcctttt accactccag cctagcccct accccccaat    9540
taggagggca ctggcccca acaggcatca ccccgctaaa tccctagaa gtcccactcc    9600
taaacacatc cgtattactc gcatcaggag tatcaatcac ctgagctcac catagtctaa   9660
tagaaaacaa ccgaaaccaa ataattcaag cactgctta tacaatttta ctgggtctct    9720
attttacct cctacaagcc tcagagtact tcgagtctcc cttcaccatt tccgacggca    9780
tctacggctc aacattttt gtagccacag gcttccacgg acttcacgtc attattggct    9840
caactttcct cactatctgc ttcatccgcc aactaatatt tcactttaca tccaaacatc   9900
actttggctt cgaagccgcc gcctgatact ggcattttgt agatgtggtt tgactatttc    9960
tgtatgtctc catctattga tgagggtctt actcttttag tataaatagt accgttaact  10020
tccaattaac tagttttgac aacattcaaa aaagagtaat aaacttcgcc ttaattttaa  10080
taatcaacac cctcctagcc ttactactaa taattattac attttgacta ccacaactca  10140
acggctacat agaaaaatcc accccttacg agtgcggctt cgaccctata tcccccgccc  10200
gcgtcccttt ctccataaaa ttcttcttag tagctattac cttcttatta tttgatctag  10260
aaattgccct cctttaccc ctaccatgag ccctacaaac aactaacctg ccactaatag   10320
ttatgtcatc cctcttatta atcatcatcc tagccctaag tctggcctat gagtgactac  10380
aaaaaggatt agactgaacc gaattggtat atagtttaaa caaacgaat gatttcgact   10440
cattaaatta tgataatcat atttaccaaa tgcccctcat ttacataaat attatactag  10500
catttaccat ctcacttcta ggaatactag tatatcgctc acacctcata tcctccctac  10560
tatgcctaga aggaataata ctatcgctgt tcattatagc tactctcata accctcaaca  10620
cccactccct cttagccaat attgtgccta ttgccatact agtctttgcc gcctgcgaag  10680
cagcggtggg cctagcccta ctagtctcaa tctccaacac atatggccta gactacgtac  10740
ataacctaaa cctactccaa tgctaaaact aatcgtccca acaattatat tactaccact  10800
gacatgactt tccaaaaaac acataatttg aatcaacaca accacccaca gcctaattat  10860
tagcatcatc cctctactat tttttaacca aatcaacaac aacctattta gctgttcccc  10920
aaccttttcc tccgaccccc taacaacccc cctcctaata ctaactacct gactcctacc  10980
cctcacaatc atggcaagcc aacgccactt atccagtgaa ccactatcac gaaaaaaact  11040
ctacctctct atactaatct ccctacaaat ctccttaatt ataacattca cagccacaga  11100
actaatcata ttttatatct tcttcgaaac cacacttatc cccaccttgg ctatcatcac  11160
ccgatgaggc aaccagccag aacgcctgaa cgcaggcaca tacttcctat tctacaccct  11220
agtaggctcc cttcccctac tcatcgcact aatttacact cacaacaccc taggctcact  11280
aaacattcta ctactcactc tcactgccca agaactatca aactcctgag ccaacaactt  11340
aatatgacta gcttacacaa tagctttat agtaaagata cctctttacg gactccactt  11400
atgactccct aaagcccatg tcgaagcccc catcgctggg tcaatagtac ttgccgcagt  11460
actcttaaaa ctaggcggct atggtataat acgcctcaca ctcattctca accccctgac  11520
aaaacacata gcctacccct tccttgtact atccctatga ggcataatta taacaagctc  11580
catctgccta cgacaaacag acctaaaatc gctcattgca tactcttcaa tcagccacat  11640
agccctcgta gtaacagcca ttctcatcca aaccccctga agcttcaccg gcgcagtcat  11700
tctcataatc gcccacgggc ttacatcctc attactattc tgcctagcaa actcaaacta  11760
```

```
cgaacgcact cacagtcgca tcataatcct ctctcaagga cttcaaactc tactcccact   11820
aatagctttt tgatgacttc tagcaagcct cgctaacctc gccttacccc ccactattaa   11880
cctactggga gaactctctg tgctagtaac cacgttctcc tgatcaaata tcactctcct   11940
acttacagga ctcaacatac tagtcacagc cctatactcc ctctacatat ttaccacaac   12000
acaatggggc tcactcaccc accacattaa caacataaaa ccctcattca cacgagaaaa   12060
caccctcatg ttcatacacc tatcccccat tctcctccta tccctcaacc ccgacatcat   12120
taccgggttt tcctcttgta aatatagttt aaccaaaaca tcagattgtg aatctgacaa   12180
cagaggctta cgaccccctta tttaccgaga aagctcacaa gaactgctaa ctcatgcccc   12240
catgtctaac aacatggctt tctcaacttt taaaggataa cagctatcca ttggtcttag   12300
gccccaaaaa ttttggtgca actccaaata aaagtaataa ccatgcacac tactataacc   12360
accctaaccc tgacttccct aattcccccc atccttacca ccctcgttaa ccctaacaaa   12420
aaaaactcat accccccatta tgtaaaatcc attgtcgcat ccacctttat tatcagtctc   12480
ttccccacaa caatattcat gtgcctagac caagaagtta ttatctcgaa ctgacactga   12540
gccacaaccc aaacaaccca gctctcccta agcttcaaac tagactactt ctccataata   12600
ttcatccctg tagcattgtt cgttacatgg tccatcatag aattctcact gtgatatata   12660
aactcagacc caaacattaa tcagttcttc aaatatctac tcatcttcct aattaccata   12720
ctaatcttag ttaccgctaa caacctattc caactgttca tcggctgaga gggcgtagga   12780
attatatcct tcttgctcat cagttgatga tacgcccgag cagatgccaa cacagcagcc   12840
attcaagcaa tcctatacaa ccgtatcggc gatatcggtt tcatcctcgc cttagcatga   12900
tttatcctac actccaactc atgagaccca caacaaatag cccttctaaa cgctaatcca   12960
agcctcaccc cactactagg cctcctccta gcagcagcag gcaaatcagc ccaattaggt   13020
ctccacccct gactcccctc agccatagaa ggccccaccc cagtctcagc cctactccac   13080
tcaagcacta tagttgtagc aggaatcttc ttactcatcc gcttccaccc cctagcagaa   13140
aatagcccac taatccaaac tctaacacta tgcttaggcg ctatcaccac tctgttcgca   13200
gcagtctgcg cccttacaca aaatgacatc aaaaaaatcg tagccttctc cacttcaagt   13260
caactaggac tcataatagt tacaatcggc atcaaccaac cacacctagc attcctgcac   13320
atctgtaccc acgccttctt caaagccata ctatttatgt gctccgggtc catcatccac   13380
aaccttaaca atgaacaaga tattcgaaaa ataggaggac tactcaaaac catacctctc   13440
acttcaacct ccctcaccat tggcagccta gcattagcag gaataccttt cctcacaggt   13500
ttctactcca aagaccacat catcgaaacc gcaaacatat catacacaaa cgcctgagcc   13560
ctatctatta ctctcatcgc tacctccctg acaagcgcct atagcactcg aataattctt   13620
ctcaccctaa caggtcaacc tcgcttcccc acccttacta acattaacga aaataacccc   13680
accctactaa accccattaa acgcctggca gccggaagcc tattcgcagg atttctcatt   13740
actaacaaca tttcccccgc atccccctc caaacaacaa tccccctcta cctaaaactc   13800
acagccctcg ctgtcacttt cctaggactt ctaacagccc tagacctcaa ctacctaacc   13860
aacaaactta aaataaaatc cccactatgc acatttatt tctccaacat actcggattc   13920
taccctagca tcacacaccg cacaatcccc tatctaggcc ttcttacgag ccaaaacctg   13980
cccctactcc tcctagacct aacctgacta gaaaagctat tacctaaaac aatttcacag   14040
caccaaatct ccacctccat catcacctca acccaaaaag gcataattaa actttacttc   14100
```

-continued

```
ctctctttct tcttcccact catcctaacc ctactcctaa tcacataacc tattcccccg  14160
agcaatctca attacaatat atacaccaac aaacaatgtt caaccagtaa ctactactaa  14220
tcaacgccca taatcataca aagcccccgc accaatagga tcctcccgaa tcaaccctga  14280
cccctctcct tcataaatta ttcagcttcc tacactatta aagtttacca caaccaccac  14340
cccatcatac tctttcaccc acagcaccaa tcctacctcc atcgctaacc ccactaaaac  14400
actcaccaag acctcaaccc ctgaccccca tgcctcagga tactcctcaa tagccatcgc  14460
tgtagtatat ccaaagacaa ccatcattcc ccctaaataa attaaaaaaa ctattaaaacc  14520 catataaccct cccccaaaat tcagaataat aacacacccg accacaccgc taacaatcaa  14580
tactaaaccc ccataaatag gagaaggctt agaagaaaac cccacaaacc ccattactaa  14640
acccacactc aacagaaaca aagcatacat cattattctc gcacggacta caaccacgac  14700
caatgatatg aaaaaccatc gttgtatttc aactacaaga acaccaatga ccccaatacg  14760
caaaactaac cccctaataa aattaattaa ccactcattc atcgacctcc ccaccccatc  14820
caacatctcc gcatgatgaa acttcggctc actccttggc gcctgcctga tcctccaaat  14880
caccacagga ctattcctag ccatgcacta ctcaccagac gcctcaaccg ccttttcatc  14940
aatcgcccac atcactcgag acgtaaatta tggctgaatc atccgctacc ttcacgccaa  15000
tggcgcctca atattctta tctgcctctt cctacacatc gggcgaggcc tatattacgg  15060
atcatttctc tactcagaaa cctgaaacat cggcattatc ctcctgcttg caactatagc  15120
aacagccttc ataggctatg tcctcccgtg aggccaaata tcattctgag gggccacagt  15180
aattacaaac ttactatccg ccatcccata cattgggaca gacctagttc aatgaatctg  15240
aggaggctac tcagtagaca gtcccaccct cacacgattc tttacctttc acttcatctt  15300
gcccttcatt attgcagccc tagcaacact ccacctccta ttcttgcacg aaacgggatc  15360
aaacaacccc ctaggaatca cctcccattc cgataaaatc accttccacc cttactacac  15420
aatcaaagac gccctcggct tacttctctt ccttctctcc ttaatgacat taacactatt  15480
ctcaccagac ctcctaggcg acccagacaa ttataccta gccaacccct aaacaccccc  15540
tccccacatc aagcccgaat gatatttcct attcgcctac acaattctcc gatccgtccc  15600
taacaaacta ggaggcgtcc ttgccctatt actatccatc ctcatcctag caataatccc  15660
catcctccat atatccaaac aacaaagcat aatatttcgc ccactaagcc aatcacttta  15720
ttgactccta gccgcagacc tcctcattct aacctgaatc ggaggacaac cagtaagcta  15780
cccttttacc atcattggac aagtagcatc cgtactatac ttcacaacaa tcctaatcct  15840
aataccaact atctccctaa ttgaaaacaa aatactcaaa tgggcctgtc cttgtagtat  15900
aaactaatac accagtcttg taaaccggag atgaaaacct ttttccaagg acaaatcaga  15960 gaaaagtct ttaactccac cattagcacc caaagctaag attctaattt aaactattct  16020 ctgttcttc atggggaagc agatttgggt accacccaag tattgactca cccatcaaca  16080
accgctatgt atttcgtaca ttactgccag ccaccatgaa tattgtacgg taccataaat  16140
acttgaccac ctgtagtaca taaaaaccca atccacatca aaacccccctc cccatgctta  16200 caagcaagta cagcaatcaa ccctcaacta tcacacatca actgcaactc caaagccacc  16260
cctcacccca taggatacca acaaacctac ccacccttaa cagtacatag tacataaagc  16320
catttaccgt acatagcaca ttacagtcaa atcccttctc gtcccccatgg atgacccccc  16380 tcagataggg gtcccttgac caccatcctc cgtgaaatca atatcccgca caagagtgct  16440
actctcctcg ctccgggccc ataacacttg ggggtagcta aagtgaactg tatccgacat  16500
```

```
ctggttccta cttcagggtc ataaagccta aatagcccac acgttccct  taaataagac    16560
atcacgatg                                                            16569
```

POLYMORPHISMS IN HUMAN MITOCHONDRIAL DNA

CROSS-REFERENCE TO RELATED APPLICATIONS

The present application derives priority from U.S. Ser. No. 60/017,203 filed May 16, 1996 and U.S. Ser. No. 60/024,206, filed Aug. 20, 1996, which are incorporated by reference in their entirety for all purposes.

STATEMENT OF GOVERNMENT INTEREST

This application was funded in part by SPIR grant no. R43HGO1481-01 and NIH grant no. 5r01HG00813. The US Government may have certain rights in this invention.

BACKGROUND

Human mitochondrial DNA (mtDNA) is information-rich, encoding some 22 tRNAs, a 12S and a 16S rRNA, and 13 polypeptides involved in oxidative phosphorylation. No introns have been detected. RNAs are processed by cleavage at tRNA sequences, and polyadenylated posttranscriptionally. In some transcripts, polyadenylation also creates the stop codon, illustrating the parsimony of coding.

A complete prototypical sequence of the human mitochondrial genome has been published. See Anderson et al., *Nature* 290, 457-465 (1981). The reported sequence in 16,569 base pairs long. There is strand asymmetry in the base compositions, with one strand (Heavy) being relatively G rich, and the other strand (Light) being C rich. The L strand is 30.9% A, 31.2% C, 13.1% G, and 24.7% T. The sequence of the L-strand is numbered arbitrarily from the MboI-5/7 boundary in the D-loop region.

A human cell may have several hundred or more mitochondria, each with more than one copy of mtDNA. Hence each cell actually contains a population of mtDNA molecules. In many individuals, the mtDNA sequence is essentially clonal. However, some individuals carry more than one mtDNA sequence, a condition known as heteroplasmy. The degree of heteroplasmy can vary from tissue to tissue. Also, the rate of replication of mtDNAs can differ and together with random segregation during cell division, can lead to changes in heteroplasmy over time.

Mitochondrial DNA is maternally inherited, and has a mutation rate estimated to be tenfold higher than single copy nuclear DNA (Brown et al., *Proc. Natl. Acad. Sci. USA* 76, 1967-1971 (1979)). Over 80% of substitutions are transitions (i.e., pyrimidine-pyrimidine or purine-purine).

The determination of a complete human mitochondrial DNA sequence over 15 years ago has had a tremendous influence on studies of human origins and evolution, and the role of mutations in degenerative diseases. Cann et al. *Nature* 325, 31-36 (1987); Zeviani, et al., *Am. J. Hum. Genet.* 47, 904-914 (1990); Wallace, *Annu. Rev. Biochem.* 61, 1175-1212 (1992); Horai et al., *Proc. Natl. Acad. Sci. USA* 92, 532-536 (1995); Hutchin & Cortopasi, *Proc. Natl. Acad. Sci. USA* 92, 6892-6895 (1995). Because of the cost and difficulty of conventional sequence analysis, most sequencing studies have focused only on two small hypervariable regions totalling ~600 bp. Greenberg et al. *Gene* 21, 33-49 (1983); Aquardo & Greenberg, *Genetics* 103, 287-312 (1983).

The present application describes sequencing of the complete mitochondrial genome of several individuals and identifies a large set of polymorphisms.

SUMMARY OF THE INVENTION

In one aspect, the invention provides nucleic acids comprising segments of human mitochondrial DNA or RNA of between 10 and 100 bases. The segments includes any one of the 182 polymorphic sites shown in Table 1. Also included are nucleic acids comprising complements of these segments. In some segments, the polymorphic site is occupied by the base described by Anderson et al., supra. In other segments, the site is occupied by a different base, particularly one of the alternative forms shown in Table 1, column 2, or 4-11.

The invention further provides allele-specific oligonucleotides for analysis of the polymorphic sites shown in Table 1. The allele specific oligonucleotides hybridize to a segment of human mitochondrial nucleic acid or its complement including a polymorphic site shown in Table 1, column 1. Such oligonucleotides can be used as probes or primers.

The invention further provides isolated nucleic acids comprising a segment of the human mitochondrial sequence described by Anderson et al., *Nature* 290, 457-465 (1981), or the complement thereof, including a polymorphic site shown in Table 1, column 1. In these nucleic acids, the polymorphic site within the segment is occupied by a base other than the base shown in Table 1, column 3 ("asn base").

The invention further provides methods of analyzing a nucleic acid. Such methods entail obtaining a mitochondrial nucleic acid from an individual, and determining a base occupying any one of the polymorphic sites shown in Table 1.

BRIEF DESCRIPTION OF THE FIGURES

FIG. 1. (A) Design of a 4L tiled array. Each position in the target sequence (upper case) (SEQ ID NO:12) is queried by a set of 4 probes on the chip (lower case), identical except at a single position, termed the substitution position, which is either A, C, G, or T (blue indicates complementarity, red a mismatch). Two sets of probes are shown, querying adjacent positions in the target (SEQ ID NOS:13-20). (B) Effect of change in the target sequence. The probes are the same as in panel A, but the target now contains a single base substitution (C, shown in green) (SEQ ID NO:21). The probe set querying the changed base still has a perfect match (the G probe). However, probes in adjacent sets that overlap the altered target position (SEQ ID NOS:22-29) now have either one or two mismatches (red), instead of zero or one, since they were designed to match the target shown in panel A. (C) Hybridization to a 4L tiled array and detection of a base change in the target. The array shown was designed to the mt1 sequence. (Upper panel) hybridization to mt1 (SEQ ID NO:12). The substitution used in each row of probes is indicated to the left of the image. The target sequence can be read 5' to 3' from left to right as the complement of the substitution base with the brightest signal. With hybridization to mt2 (lower panel) (SEQ ID NO:21), which differs from mt1 in this region by a T→C transition, the G probe at position 16,493 is now a perfect match, with the other three probes having single base mismatches (A 5, C 3, G 37, T 4 counts). However, at flanking positions, the probes have either single or double base mismatches, since the mt2 transition now occurs away from the query position.

DEFINITIONS

Figure 2:
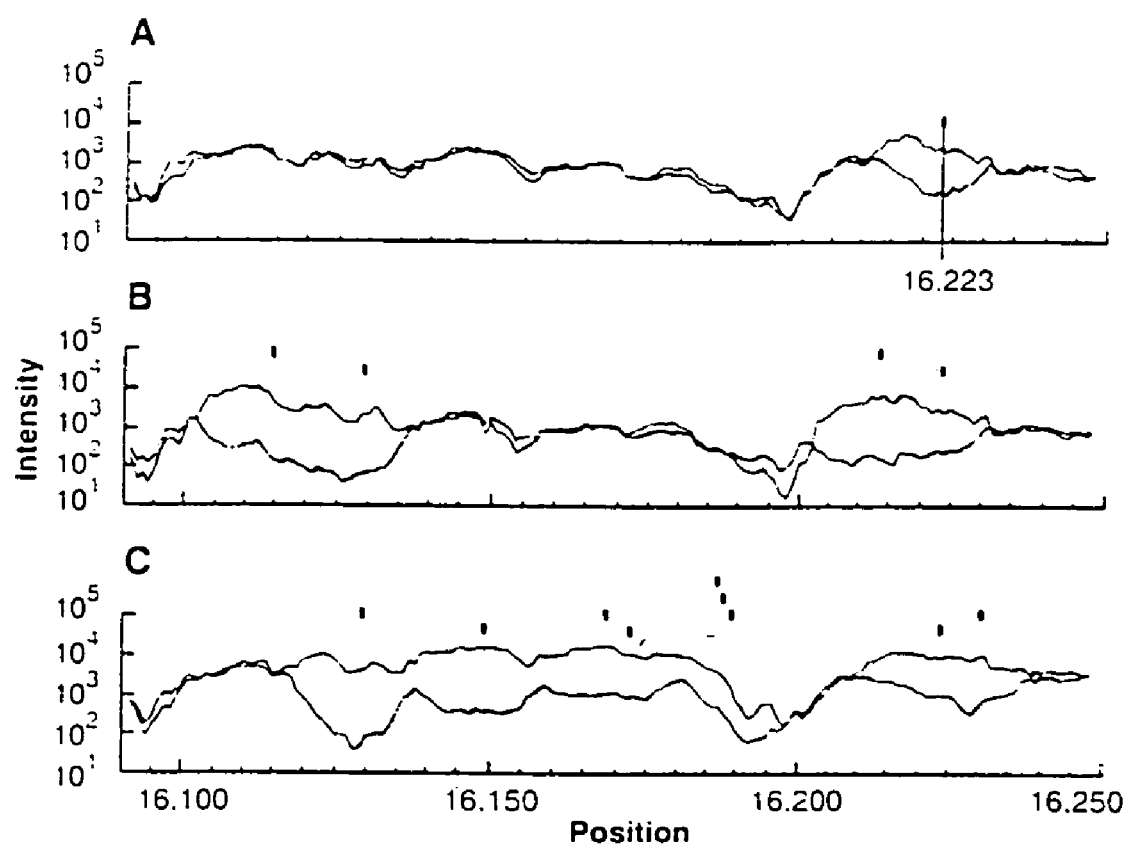
FIG. 2. Detection of base differences in a 2.5 kb region by comparison of scaled $P^o$ hybridization intensity patterns between a sample (green) and a reference (red). (A) Comparison of ief007 to mt1. In the region shown, there is a single base difference between the two sequences, located at position 16,223 (mt1 C: ief007 T). This results in a "footprint" spanning ~20 positions, 11 to the left and 8 to the right of position 16,223, in which the ief007 $P^0$ intensities are decreased by a factor of more than 10 on average relative to the mt1 intensities. The predicted footprint location is indicated by the gray bar, and the location of the polymorphism is shown by a vertical black line within the bar. (B) Comparison of ha001 to mt1. The ha001 target has 4 polymorphisms relative to mt1. The $P^0$ intensity pattern clearly shows two regions of difference between the targets. Each region contains at least 2 differences, because in both cases the footprints are longer than 20 positions, and therefore are too extensive to be explained by a single base difference. The effect of competition can be seen by comparing the mt1 intensities in the ief007 and ha001 experiments: the relative intensities of mt1 are greater in panel B where ha001 contains $P^0$ mismatches but ief007 does not. (C) The ha004 sample has multiple differences to mt1, resulting in a complex pattern extending over most of the region shown. Thus, differences are clearly detected. Because hybridization intensities are extremely sequence dependent, each of the mitochondrial sequences can also be identified simply by its hybridization pattern.

Nucleic acids, including oligonucleotides, can be DNA or RNA, and single- or double-stranded. Oligonucleotides can be naturally occurring or synthetic, but are typically prepared by synthetic means. Preferred oligonucleotides of the invention include segments of DNA, or their complements including any one of the polymorphic sites shown in Table 1. The segments are usually between 5 and 100 bases, and often between 5-10, 5-20, 10-20, 10-50, 20-50 or 20-100 bases. The polymorphic site can occur within any position of the segment. The segments can be from any of the allelic forms of DNA shown in Table 1.

Hybridization probes are oligonucleotides capable of binding in a base-specific manner to a complementary strand of nucleic acid. Such probes include peptide nucleic acids, as described in Nielsen et al., *Science* 254, 1497-1500 (1991).

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term primer site refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified.

Linkage describes the tendency of genes, alleles, loci or genetic markers to be inherited together as a result of their location on the same chromosome, and can be measured by percent recombination between the two genes, alleles, loci or genetic markers.

Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as a the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A single nucleotide polymorphism occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

Hybridizations are usually performed under stringent conditions, for example, at a salt concentration of no more than 1 M and a temperature of at least 25° C. For example, conditions of 5X SSPE (750 mM NaCl, 50 mM NaPhosphate, 5 mM EDTA, pH 7.4) and a temperature of 25-30° C. are suitable for allele-specific probe hybridizations.

An isolated nucleic acid means an object species invention that is the predominant species present (i.e., on a molar basis it is more abundant than any other individual species in the composition). Preferably, an isolated nucleic acid comprises at least about 50, 80 or 90 percent (on a molar basis) of all macromolecular species present. Most preferably, the object species is purified to essential homogeneity (contaminant species cannot be detected in the composition by conventional detection methods).

DETAILED DESCRIPTION

I. Novel Polymorphisms of the Invention

The present application provides the location of 505 polymorphisms at 182 sites in human mitochondrial DNA (see attached Table 1). The first column of the table identifies the position of polymorphisms according to a convention whereby nucleotides in the mitochondrial genomes of different individuals are assigned the same number as the corresponding nucleotide in the sequence of Anderson et al., supra when the two sequences are maximally aligned. For example, reading from the top of the table, polymorphisms occur at positions 63, 72, 92, 181, 194 and so on. The column headed rbase indicates the base occupying the position in a mitochondrial reference sequence whose sequence was determined by ABI sequencing. The column headed asn-base indicates the base occupying the position in the published sequence of Anderson et al. (1981), supra. The remaining columns in the table indicate the base present at the polymorphic position in each of 10 African individuals (designated from left to right HA001, HA002, HA004 and so forth). Upper case letters indicate that the base occupying a polymorphic position has been established with substantial certainty in an individual. Lower case letters indicate that although the existence of a polymorphic position is certain, there is a possibility of experimental error in determining the base indicated as occupying that position in an individual. The letter "n" indicates that the base occupying a position in an individual was ambiguous. Some ambiguities may be due to heteroplasmy.

The polymorphic sites listed in the table are widely distributed throughout the mitochondrial genome, and occur in many of the known genes within the genome (i.e., 22 tRNAs, a 12S and a 16S rRNA, and 13 polypeptides involved in oxidative phosphorylation). The polymorphic sites can be classified in sets according to which gene the polymorphic site occurs.

II. Analysis of Polymorphisms

A. Preparation of Samples

Polymorphisms are detected in a target nucleic acid from an individual being analyzed. For assay of mitochondrial DNA, virtually any biological sample is suitable. For example, convenient tissue samples include whole blood, semen, saliva, tears, urine, fecal material, sweat, buccal, skin and hair.

Amplification of nucleic acids from target samples is sometimes desirable and can be accomplished by e.g., PCR. See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (eds. McPherson et al., IRL Press, Oxford); and U.S. Pat. No. 4,683,202 (each of which is incorporated by reference for all purposes).

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Amplification is not always necessary in view of the multiple copies of mitochondrial DNA in a single cell. Analysis without amplification is preferred for analysis of relative levels of various mitochondrial DNA subpopulations, such as mitochondrial DNAs bearing deletions, without affecting their relative levels.

B. Detection of Polymorphisms in Target DNA

There are two distinct types of analysis depending whether a polymorphism in question has already been characterized. The first type of analysis is sometimes referred to as de novo characterization. This analysis compares target sequences in different individuals to identify points of variations, i.e., polymorphic sites. By analyzing a groups of individuals representing the greatest ethnic diversity among humans and greatest breed and species variety in plants and animals, patterns characteristic of the most common alleles/haplotypes of the locus can be identified, and the frequencies of such populations in the population determined. Additional allelic frequencies can be determined for subpopulations characterized by criteria such as geography, race, or gender. The de novo identification of the polymorphisms of the invention is described in the Examples section. The second type of analysis is determining which form(s) of a characterized polymorphism are present in individuals under test. There are a variety of suitable procedures, which are discussed in turn.

1. Allele-Specific Probes

The design and use of allele-specific probes for analyzing polymorphisms is described by e.g., Saiki et al., *Nature* 324, 163-166 (1986); Dattagupta, EP 235,726, Saiki, WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15 mer at the 7 position; in a 16 mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of proves can then be immobilized on the same support for simultaneous analysis of multiple polymorphisms within the same target sequence.

2. Tiling Arrays

The polymorphisms can also be identified by hybridization to nucleic acid arrays, some example of which are described by WO 95/11995 (incorporated by reference in its entirety for all purposes). One form of such arrays is described in the Examples section in connection with de novo identification of polymorphisms. The same array or a different array can be used for analysis of characterized polymorphisms. WO 95/11995 also describes subarrays that are optimized for detection of a variant forms of a precharacterized polymorphism. Such a subarray contains probes designed to be complementary to a second reference sequence, which is an allelic variant of the first reference sequence. The second group of probes is designed by the same principles as described in the Examples except that the probes exhibit complementarily to the second reference sequence. The inclusion of a second group (or further groups) can be particular useful for analyzing short subsequences of the primary reference sequence in which multiple mutations are expected to occur within a short distance commensurate with the length of the probes (i.e., two or more mutations within 9 to 21 bases).

3. Allele-Specific Primers

An allele-specific primer hybridizes to a site on target DNA overlapping a polymorphism and only primes amplification of an allelic form to which the primer exhibits perfect complementarily. See Gibbs, *Nucleic Acid Res.* 17, 2427-2448 (1989). This primer is used in conjunction with a second primer which hybridizes at a distal site. Amplification proceeds from the two primers leading to a detectable product signifying the particular allelic form is present. A control is usually performed with a second pair of primers, one of which shows a single base mismatch at the polymorphic site and the other of which exhibits perfect complementarily to a distal site. The single-base mismatch prevents amplification and no detectable product is formed. The method works best when the mismatch is included in the 3'-most position of the oligonucleotide aligned with the polymorphism because this position is most destabilizing to elongation from the primer. See, e.g., WO 93/22456.

4. Direct-Sequencing

The direct analysis of the sequence of polymorphisms of the present invention can be accomplished using either the dideoxy chain termination method or the Maxam Gilbert method (see Sambrook et al., *Molecular Cloning, A Laboratory Manual* (2nd Ed., CSHP, New York 1989); Zyskind et al., *Recombinant DNA Laboratory Manual*, (Acad. Press, 1988)).

5. Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoresis migrating of DNA in solution. Erlich, ed., *PCR Technology, Principles and Applications for DNA Amplification*, (W. H. Freeman and Co, New York, 1992), Chapter 7.

6. Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., *Proc. Nat. Acad. Sci.* 86, 2766-2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence differences between alleles of target sequences.

III. Methods of Use

After determining polymorphic form(s) present in an individual at one or more polymorphic sites, this information can be used in a number of methods.

A. Forensics

Determination of which polymorphic forms occupy a set of polymorphic sites in an individual identifies a set of polymorphic forms that distinguishes the individual. See generally National Research Council, *The Evaluation of Forensic DNA Evidence* (Eds. Pollard et al., National Academy Press, DC, 1996). The more sites that are analyzed the lower the probability that the set of polymorphic forms in one individual is the same as that in an unrelated individual. Preferably, if multiple sites are analyzed, the sites are unlinked. Thus, polymorphisms of the invention are often used in conjunction with polymorphisms in distal genes. Preferred polymorphisms for use in forensics are diallelic because the population frequencies of two polymorphic forms can usually be determined with greater accuracy than those of multiple polymorphic forms at multi-allelic loci.

The capacity to identify a distinguishing or unique set of forensic markers in an individual is useful for forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers does match, one can conclude that the DNA from the suspect is consistent with that found at the crime scene. If frequencies of the polymorphic forms at the loci tested have been determined (e.g., by analysis of a suitable population of individuals), one can preform a statistical analysis to determine the probability that a match of suspect and crime scene sample would occur by chance.

B. Correlation of Polymorphisms with Phenotypic Traits

The polymorphisms of the invention may contribute to the phenotype of an organism in different ways. Some polymorphisms occur within a protein coding sequence and contribute to phenotype by affecting protein structure. The defect may be neutral, beneficial or detrimental, or both beneficial and detrimental, depending on the circumstances. Other polymorphisms occur in noncoding regions but may exert phenotypic effects indirectly via influence on replication, transcription, and translation. A single polymorphism may affect more than one phenotypic trait. Likewise, a single phenotypic rate may be affected by polymorphisms in different genes. Further, some polymorphisms predispose an individual to a distinct mutation that is causally related to a certain phenotype.

Some disease traits are already known to be mitochondrially inherited. Some such disease traits result, at least in part, from stop codons in structural genes. Such mutations have been mapped and associated with diseases, such as Leber's hereditary optic neuropathy, neurogenic muscular weakness, ataxia and retinitis pigmentosa. Other mutations (nucleotide substitutions) occur in tRNA coding sequences, and presumably cause conformational defects in transcribed tRNA molecules. Such mutations have also been mapped and associated with diseases such as Myoclonic Epilepsy and Ragged Red Fiber Disease. See Wallace, *Ann. Rev. Biochem.* 61, 1175-1212 (1992) (incorporated by reference in its entirety for all purposes).

Other genetic diseases having hitherto unmapped genetic component(s) may also result in part from variations in mitochondrial DNA. Candidate diseases include, e.g., agammaglobulimenia, diabetes insipidus, Lesch-Nyhan syndrome, muscular dystrophy, Wiskott-Aldrich syndrome, Fabry's disease, familial hypercholesterolemia, polycystic kidney disease, hereditary spherocytosis, von Willebrand's disease, tuberous sclerosis, hereditary hemorrhagic telangiectasia, familial colonic polyposis, Ehlers-Danlos syndrome, osteogenesis imperfecta, and acute intermittent porphyria).

Other phenotypic traits that may derive, at least in part, from variations in mitochondrial DNA include symptoms of, or susceptibility to, multifactorial diseases of which a component is or may be genetic, such as Alzheimer's disease, autoimmune diseases, inflammation, cancer, diseases of the nervous system, and infection by pathogenic microorganisms. Some examples of autoimmune diseases include rheumatoid arthritis, multiple sclerosis, diabetes (insulin-dependent and non-independent), systemic lupus erythematosus and Graves disease. Some examples of cancers includes cancers of the bladder, brain, breast, colon, esophagus, kidney, leukemia, liver, lung, oral cavity, ovary, pancreas, prostate, skin, stomach and uterus. Phenotypic traits also include characteristics such as longevity, appearance (e.g., baldness, obesity), strength, speed, endurance, fertility, and susceptibility or receptivity to particular drugs or therapeutic treatments.

Correlation is performed for a population of individuals who have been tested for the presence or absence of a phenotypic trait of interest and for polymorphic markers sets. To perform such analysis, the presence or absence of a set of polymorphisms (i.e. a polymorphic set) is determined for a set of the individuals, some of whom exhibit a particular trait, and some of whom exhibit lack of the trait. The alleles of each polymorphism of the set are then reviewed to determine whether the presence or absence of a particular allele is associated with the trait of interest. Correlation can be performed by standard statistical methods such as a κ-squared test and statistically significant correlations between polymorphic form(s) and phenotypic characteristics are noted. For example, it might be found that the presence of allele A1 at polymorphism A correlates with heart disease. As a further example, it might be found that the combined presence of allele A1 at polymorphism A and allele B1 at polymorphism B correlates with increased milk production in a mother after birth of a child.

Such correlations can be exploited in several ways. In the case of a strong correlation between a set of one or more polymorphic forms and a disease for which treatment is available, detection of the polymorphic form set in a human or animal patient may justify immediate administration of treatment, or at least the institution of regular monitoring of the patient, before irretrievable damage has occurred. Treatments include metabolic replacement and gene therapy. See Wallace, supra. Detection of a polymorphic form correlated with serious disease in a couple contemplating a family may also be valuable to the couple in their reproductive decisions. For example, the female partner might elect to undergo in vitro fertilization to avoid the possibility of transmitting such a polymorphism from her husband to her offspring. In the case of a weaker, but still statistically significant correlation between a polymorphic set and human disease, immediate therapeutic intervention or monitoring may not be justified. Nevertheless, the patient can be motivated to begin simple life-style changes (e.g., diet, exercise) that can be accomplish at little cost to the patient but confer potential benefits in reducing the risk of conditions to which the patient may have increased susceptibility by virtue of variant alleles. Identification of a polymorphic set in a patient correlated with enhanced receptiveness to one of several treatment regimes for a disease indicates that this treatment regime should be followed.

As an example of how mitochondrial polymorphisms can be correlated with phenotypic traits, Beitz et al., U.S. Pat. No. 5,292,639 discuss use of bovine mitochondrial polymorphisms in a breeding program to improve milk production in cows. To evaluate the effect of mtDNA D-loop sequence polymorphism on milk production, each cow was assigned to value of 1 if variant or 0 if wildtype with respect to a prototypical mitochondrial DNA sequence at each of 17 locations considered. Each production trait was analyzed individually with the following animal model:

$$Y_{ijkpn} = \mu + YS_i + P_j + X_k + \beta_1 + \ldots \beta_{17} + PE_n + a_n + e_p$$

where $Y_{ijknp}$ is the milk, fat, fat percentage, SNF, SNF percentage, energy concentration, or lactation energy record; $\mu$ is an overall mean; $YS_i$ is the effect common to all cows calving in year-season; $X_k$ is the effect common to cows in either the high or average selection line; $\beta_1$ to $\beta_{17}$ are the binomial regressions of production record on mtDNA D-loop sequence polymorphisms; $PE_n$ is permanent environmental effect common to all records of cow n; $a_n$ is effect of animal n and is composed of the additive genetic contribution of sire and dam breeding values and a Mendelian sampling effect; and $e_p$ is a random residual. It was found that eleven of seventeen polymorphisms tested influenced at least one production trait. Bovines having the best polymorphic forms for milk production at these eleven loci are used as parents for breeding the next generation of the herd.

IV. Modified Polypeptides and Gene Sequences

The invention further provides variant forms of nucleic acids and corresponding proteins. The nucleic acids comprise a segment of at least 10 bases of the nucleotide sequence of Anderson, supra, except at one of the polymorphic positions described in Table 1, column 1, in which the polymorphic position is occupied by a different base than described by Anderson, supra. Preferably, the different base is one of the alternative bases for that position shown in Table 1. Some nucleic acid encode full-length variant forms of proteins. Similarly, variant proteins have the prototypical amino acid sequences of proteins encoded by the nucleic acid sequence of Anderson, supra, (read in-frame) except at an amino acid encoded by a codon including one of the polymorphic positions shown in Table 1. That position is occupied by a different amino acid than described by Anderson, supra, and preferably an amino acid encoded by a corresponding codon of any of the alternative forms for the position shown in the Table.

Variant genes can be expressed in an expression vector in which a variant gene is operably linked to a native or other promoter. Usually, the promoter is a eukaryotic promoter for expression in a mammalian cell. The transcription regulation sequences typically include a heterologous promoter and optionally an enhancer which is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The means of introducing the expression construct into a host cell varies depending upon the particular construction and the target host. Suitable means include fusion, conjugation, transfection, transduction, electroporation or injection, as described in Sambrook, supra. A wide variety of host cells can be employed for expression of the variant gene, both prokaryotic and eukaryotic. Suitable host cells include bacteria such as E. coli, yeast, filamentous fungi, insect cells, mammalian cells, typically immortalized, e.g., mouse, CHO, human and monkey cell lines and derivatives thereof. Preferred host cells are able to process the variant gene product to produce an appropriate mature polypeptide. Processing includes glycosylation, ubiguitination, disulfide bond formation, general post-transitional modification, and the like.

The protein may be isolated by conventional means of protein biochemistry and purification to obtain a substantially pure product, i.e., 80, 95 or 99% free of cell component contaminants, as described in Jacoby, *Methods in Enzymology* Volume 104, Academic Press, New York (1984); Scopes, *Protein Purification, Principles and Practice*, 2nd Edition, Springer-Verlag, New York (1987); and Deutscher (ed), *Guide to Protein Purification, Methods in Enzymology*, Vol. 182 (1990). If the protein is secreted, it can be isolated from the supernatant in which the host cell is grown. If not secreted, the protein can be isolated from a lysate of the host cells.

The invention further provides transgenic nonhuman animals capable of expressing an exogenous variant gene and/or having one or both alleles of an endogenous variant gene inactivated. Expression of an exogenous variant gene is usually achieved by operably linking the gene to a promoter and optionally an enhancer, and microinjecting the construct into a zygote. See Hogan et al., "Manipulating the Mouse Embryo, A Laboratory Manual," Cold Spring Harbor Laboratory. Inactivation of endogenous variant genes can be achieved by forming a transgene in which a cloned variant gene is inactivated by insertion of a positive selection marker. See Capecchi, *Science* 244, 1288-1292 (1989). The transgene is then introduced into an embryonic stem cell, where it undergoes homologous recombination with an endogenous variant gene. Mice and other rodents are preferred animals. Such animals provide useful drug screening systems.

In addition to substantially full-length polypeptides expressed by variant genes, the present invention includes biologically active fragments of the polypeptides, or analogs thereof, including organic molecules which simulate the interactions of the peptides. Biologically active fragments include any portion of the full-length polypeptide which confers a biological function on the variant gene product, including ligand binding, and antibody binding. Ligand binding includes binding by nucleic acids, proteins or polypeptides, small biologically active molecules, or large cellular structures.

Polyclonal and/or monoclonal antibodies that specifically bind to variant gene products but not to corresponding prototypical gene products are also provided. Antibodies can be made by injecting mice or other animals with the variant gene product or synthetic peptide fragments thereof. Monoclonal antibodies are screened as are described, for example, in Harlow & Lane, *Antibodies, A Laboratory Manual*, Cold Spring Harbor Press, New York (1988); Goding, *Monoclonal antibodies, Principles and Practice* (2d ed.) Academic Press, New York (1986). Monoclonal antibodies are tested for specific immunoreactivity with a variant gene product and lack of immunoreactivity to the corresponding prototypical gene product. These antibodies are useful in diagnostic assays for detection of the variant form, or as an active ingredient in a pharmaceutical composition.

V. Kits

The invention further provides kits comprising at least one allele-specific oligonucleotide as described above. Often, the kits contain one or more pairs of allele-specific oligonucleotides hybridizing to different forms of a polymorphism. In some kits, the allele-specific oligonucleotides are provided immobilized to a substrate. For example, the same substrate can comprise allele-specific oligonucleotide probes for detecting at least 10, 100 or all of the polymorphisms shown in Table 1. Optional additional components of the kit include, for example, restriction enzymes, reverse-transcriptase or polymerase, the substrate nucleoside triphosphates, means used to label (for example, an avidin-enzyme conjugate and enzyme substrate and chromogen if the label is biotin), and the appropriate buffers for reverse transcription, PCR, or hybridization reactions. Usually, the kit also contains instructions for carrying out the methods.

EXAMPLES

An array consisting of oligonucleotides complementary to subsequences of a target sequence can be used to determine the identity of a target sequence, measure its amount, and detect differences between the target and a reference sequence. Many different arrays can be designed for these purposes. One such design, termed a 4L tiled array, is depicted schematically in FIG. 1A. In each set of four probes, the perfect complement will hybridize more strongly than mismatched probes. By this approach, a nucleic acid target of length L can be scanned for mutations with a tiled array containing 4L probes. For example, to query the 16,569 bp of human mitochondrial DNA (mtDNA), only 66,276 probes of the possible $\sim 10^9$ 15-mers need to be used.

The use of a tiled array of probes to read a target sequence is illustrated in FIG. 1C. A tiled array of 15-mers varied at position 7 from the 3' end ($P^{15,7}$) was designed and synthesized for mt1, a cloned sequence containing 1,311 bp spanning the control region of mtDNA (Anderson, et al., *Nature* 290, 457-465 (1981); Greenberg et al., *Gene* 21, 33-49 (1983); Aquardo & Greenberg, *Genetics* 103, 287-312 (1983); Cann et al. *Genetics* 106, 479-499 (1984).

The mt1 and mt2 sequences were cloned from amplified genomic DNA extracted from hair roots (Gill et al. *Nature* 318, 577-579 (1985); Saiki, et al., *Science* 239, 487-491 (1988)). The clones were sequenced conventionally. Cloning was performed only to provide a set of pure reference samples of known sequence. To provide templates for fluorescent labeling, DNA was reamplified from the clones using primers bearing bacteriophage T3 and T7 RNA polymerase promoter sequences (bold; mtDNA sequences uppercase): L15935-T3, 5'ctcggaattaaccctcactaaaggAAAC-CTTTTTCCAAGGA (SEQ ID NO:1) and H667-T7, 5'taatacgactcactatagggagAGGCTAGGACCAAACCTATT (SEQ ID NO:2).

The upper panel of FIG. 1C shows a portion of the fluorescence image of an array hybridized with fluorescein-labeled mt1 RNA. Labeled RNAs from the two complementary 2mtDNA strands (designated L and H) were transcribed in separate reactions from a promoter-tagged PCR product. Each 10 µl reaction contained 1.5 mM each of ATP, CTP, GTP and UTP, 0.24 mM fluorescein-12-CTP (Du Pont), 0.24 mM fluorescein-12-UTP (Boehringer Mannheim), $\sim 1$ to 5 nM (1.5 µl) crude unpurified 1.3 kb PCR product and 1 unit/ml T3 or T7 RNA polymerase (Promega), in a reaction buffer supplied with the enzyme. The reaction was carried out at 37° C. for 1 to 2 h. RNA was fragmented to an average size of <100 nt by adjusting the solution to 30 mM $MgCl_2$, by the addition of 1 M MgCl$_2$, and heating at 94° C. for 40 minutes. Fragmentation improved the uniformity and specificity of hybridization. The extent of fragmentation is dependent on magnesium ion concentration [Huff et al., Biochem. 3, 501-506 (1964); Butzow et al. Biopolymers 3, 95-107 (1965)]. Good hybridization results have been obtained with both DNA and RNA targets prepared using a variety of labelling schemes, including incorporation of fluorescent and biotinylated dNTPs by DNA polymerases, incorporation of dye-labelled primers during PCR, ligation of labelled oligonucleotides to fragmented RNA, and direct labelling by photo-crosslinking a psoralen derivative of biotin directly to fragmented nucleic acids.

The base sequence can be read by comparing the intensities of the four probes within each column. For example, the column for position 16,493 consists of the four probes, 3'-TGACAT$\underline{A}$GGCTGTAG (SEQ ID NO:3), 3'-TGACAT$\underline{C}$GGCTGTAG (SEQ ID NO:4), 3'-TGACAT$\underline{G}$GGCTGTAG (SEQ ID NO:5), and 3'-TGACAT$\underline{T}$GGCTGTAG (SEQ ID NO:6). The probe with the strongest signal is the probe with the $\underline{A}$ substitution ($\underline{A}$ 49, $\underline{C}$ 8, $\underline{G}$ 15, $\underline{T}$ 8 counts, 2 counts background), identifying the base at position 16,493 as U in the RNA transcript. Continuing the process, the sequence at each position can be read directly from the hybridization intensities.

The effect on the array hybridization pattern caused by a single base change in the target is shown in FIG. 1B, and the detection of a single-base polymorphism is shown in the lower panel of FIG. 1C. The target here is mt2, which differs from mt1 in this region by a T to C transition at position 16,493. Accordingly, the probe with the $\underline{G}$ substitution (third row) displays the strongest signal. Since the tiled array was designed to mt1, the hybridization intensities of neighboring probes that overlap 16,493 are also affected by the change in target sequence. The hybridization signals of 60 probes (4×15) of the 15-mer tiled array are perturbed by a single-base change in the target sequence. In the $P^{15,7}$ array, each probe querying the 8 positions to the left and 6 positions to the right of the polymorphism contain at least one mismatch to the target. The result is a characteristic loss of signal or a "footprint" for the probes flanking a mutation position. Of the four probes querying each position, the loss of signal is greatest for the one designed to match mt1. We donote the subset of probes with zero mismatches to the reference sequence as $P^0$.

A comparison of $P^0$ hybridization signals from a target to those from a reference is ideally obtained by hybridizing both samples to the same arrays. We therefore developed a two-color labeling and detection scheme in which the reference is labeled with phycoerythrin (red), and the target with fluorescein (green). The reference and unknown samples were labeled with biotin and fluorescein, respectively, in separate transcription reactions. Reactions were carried out as described above except that each contained 1.25 mM of ATP, CTP, GTP and UTP and 0.5 mM fluorescein-12-UTP or 0.25 mM biotin-16-UTP (Boehringer Mannheim). The two reactions were mixed in the ratio 1:5 (v/v) biotin:fluorescein and fragmented. Targets were diluted to a final concentration of ⁻100 to 1000 pM in 3 M TMAC1 [Melchior et al., Proc. Natl. Acad. Sci. USA 70, 298-302 (1973)], 10 mM Tris.Cl pH 8.0, 1 mM EDTA, 0.005% Triton X-100, and 0.2 nM of a control oligonucleotide, 5' fluorescein-CTGAACGGTAGCATCTTGAC (SEQ ID NO:7). Samples were denatured at 95° C. for 5 min, chilled on ice for 5 min and equilibrated to 37° C. A volume of 180 µl of hybridization solution was then added to the flow cell [Lipshutz et al., Biotechniques 19, 442-447 (1995)], and the chip incubated at 37° C. for 3 h with rotation at 60 rpm. The chip was washed 6 times at RT with 6×SSPE, 0.005% Triton X-100. Phycoerythrin-conjugated streptavidin (2 µg/ml in 6×SSPE, 0.005% Triton X-100) was added and incubation continued at RT for 5 min. The chip was washed again, and rscanned at a resolution of ⁻74 pixels per probe cell. Two scans were collected, a fluorescein scan using a 515 to 545 nm bandpass filter, and a phycoerythrin scan using a 560 nm longpass filter. Signals were separated to remove spectral overlap and average counts per cell determined.

By processing the reference and target together, experimental variability during the fragmentation, hybridization, washing, and detection steps is minimized or eliminated. In addition, during co-hybridization of the reference and target, competition for binding sites results in a slight improvement in mismatch discrimination. However, array hybridization is highly reproducible, and comparative analysis of data obtained from separate but identically synthesized arrays is also effective.

The two-color approach was tested by analyzing a 2.5 kb region of mtDNA, that spans the tRNA$^{Glu}$, cytochrome b, tRNA$^{Thr}$, tRNA$^{Pro}$, control region and tRNA$^{Phe}$ DNA sequences. Each 2.5 kb target sequence was PCR amplified directly from genomic DNA using the primer pair L14675-T3 (5'aattaaccctcactaaagggATTCTCG-CACGGACTACAAC) (SEQ ID NO:8) and H667-T7. A $P^{20,9}$ array (i.e., containing 20-mer probes varied at position 9 from the 3' end) was designed to match the mt1 target (i.e., $P^0$ sequence=mt1). The mt1 reference (red) and a polymorphic target sample (green) were pooled and hybridized simultaneously to the array. Differences between the target and references sequence were identified by comparing the scaled red and green $P^0$ hybridization intensities. To scale the sample to the reference intensities, a histogram of the base 10 logarithm of the intensity ratios for each pair of probes was constructed. The histogram had a mesh size of 0.01, and was smoothed by replacing the value at each point with the average number of counts over a five-point window centered at that point. The highest value in the histogram was located, and the resulting intensity ratio was taken to be the most probable calibration coefficient.

The marked decrease in target hybridization intensity, over a span ⁻20 nucleotides, is shown for a single base polymorphism at position 16,223 (FIG. 2A). The footprint is enlarged when two polymorphisms occur in close proximity (within ⁻20 nucleotides) as shown in FIG. 2B. When polymorphisms are clustered, the size of the footprint depends on the number of polymorphisms and their separation (FIG. 2C).

Polymorphisms, particularly multiple polymorphisms within a probe length, can be read most accurately by combining the results of basecalling and footprinting. Closely spaced multiple polymorphisms are easily identified by the presence of a large footprint (FIGS. 2B and C) or by two or more basecalls differing from $P^0$ within a single probe span. Discrepancies between basecalling and footprint patterns are flagged for further analysis (for example, a $P^0$ footprint in which no polymorphism is identified: such a pattern is typical of a deletion). Thus, basecalls are valid only for unflagged regions. In flagged regions, the presence of sequence differences is detected, but no attempt is made to call the sequence without further analysis.

Sequence analysis was carried out on the 2.5 kb target from 12 samples. A total of 30,582 bp containing 180 substitutions relative to mt1 was analyzed. 98% of the sequence was unambiguously assigned by a Bayesian basecalling algorithm. Base identification was accomplished using a Bayesian classification algorithm based on variable kernel density estimation. The likelihood of each basecall associated with a set of hybridization intensity values was computed by comparing an unknown set of probes to a set of example cases for which the correct basecall was known. The resulting four likelihoods were then normalized so that they summed to 1. Data from both strands were combined by averaging the values. If the most likely basecall has an average normalized likelihood greater than 0.6, it was called, otherwise the base was called as an ambiguity. The example set was derived from 2 different samples, ib013 and ief005, which have a total of 35 substitutions relative to mt1, of which 19 are shared with the 12 samples analyzed and 16 are not. Basecalling performance was not sensitive to the choice of examples. Of this 98%, which contained both wild-type sequence and a high proportion of single-base footprints such as the example showing in FIG. 2A, 29,878 out of 29,879 bp were called correctly.

To provide an independently determined reference sequence, each 2.5 kb PCR amplicon was sequenced on both strands by primer-directed fluorescent chain-terminator cycle sequencing using an ABI 373A DNA sequencer, and assembled and manually edited using Sequencer 3.0. The analysis presented here assumes that the sequence amplified from genomic DNA is essentially clonal [Monnat & Loeb, *Proc. Natl. Acad. Sci. USA* 82, 2895-2899 (1985)], and that its determination by gel-based methods is correct. A common length polymorphism at positions 303-309 was not detected by hybridization under the conditions used. It was excluded from analysis, and is not part of the set of 180 polymorphisms discussed in the text. However, polymorphisms at this site have previously been differentiated by oligonucleotide hybridization [Stoneking et al., *Am. J. Hum. Genet.* 48, 370-382 (1991)].

The remaining 2%, that contained the multiple substitution footprints (such as those shown in FIGS. 2B and 2C), was flagged for further analysis. Of the 649 bp comprising this 2%, 643 bp were located in or immediately adjacent to footprints. The $P^0$ intensity footprints were detected in the following way: the reference and sample intensities were normalized (15), and R, the average of $\log_{10}$ ($P^0$ reference/$P^0$ sample) over a window of 5 positions, centered at the base of interest, calculated for each position in the sequence. Footprints were detected as regions having at least 5 contiguous positions with a reference or sample intensity at least 50 counts above background, and an R value in the top 10th percentile for the experiment. At 205 polymorphic sites, where the sample was mismatched to $P^0$, the mean R value was 1.01, with a standard deviation of 0.57. At 35,333 non polymorphic sites (i.e. where both reference and sample had a perfect match to $P^0$) the mean value was −0.05, with a standard deviation of 0.25.

In all, 179 out of the 180 polymorphisms were unambiguously detected; 126 out of 127 were called correctly in the unflagged regions; and 53 polymorphisms occurring in the flagged regoins were detected as footprints. There were no false positive basecalls, and only one false positive footprint. These figures can be considered to be "worst case" estimates for the type of array and target used. The $P^0$ sequence represents a Caucasian haplotype, and our sample set included 8 African samples having a large number of clustered differences to $P^0$. Furthermore, the variation in the hypervariable part of the control region is much higher than for the rest of the mitochondrial genome and for nuclear genes in general (FIGS. 2A, B and C show comparisons to African samples in this region).

Figure 3:
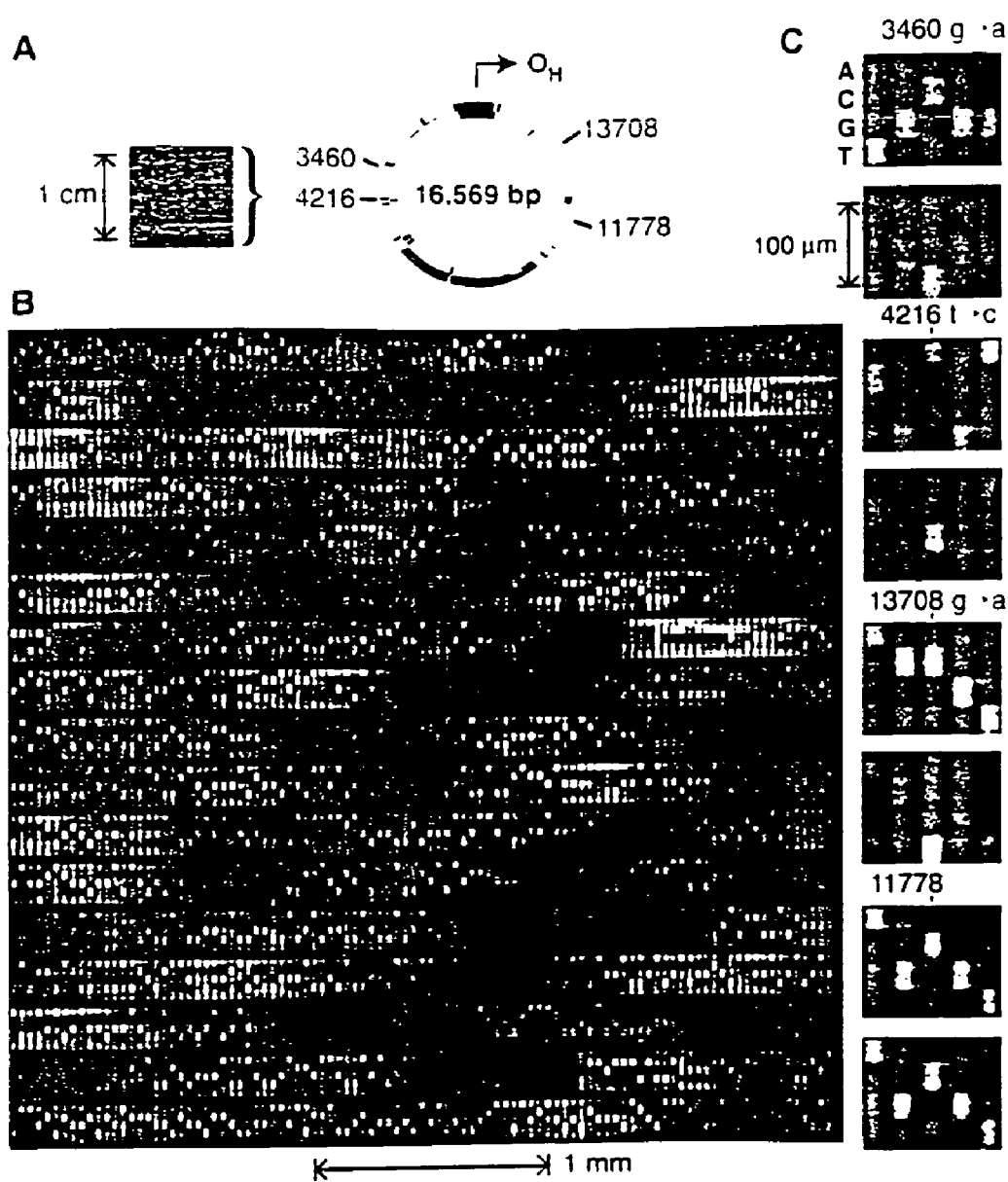
FIG. 3. Human mitochondrial genome on a chip. (A) An image of the array hybridized to a 16.6 kb L strand mitochondrial target RNA. The 16,569 bp map of the genome is shown and the H strand origin of replication ($O_H$), located in the control region, is indicated. (B) A portion of the hybridization patter, magnified. In each column there are 5 probes: A, C, G, T and D, from top to bottom. The D probe has a single base deletion instead of a substitution, and hence is 24 instead of 25 bases in length. The scale is indicated by the bar beneath the image. Although there is considerable intensity variation, most of the array can be read directly. The image was collected at a resolution of ~100 pixels per probe cell. (C) The ability of the array to detect and read signal base differences in a 16.6 kb sample is illustrated. Two different target sequences were hybridized in parallel to different chips. The hybridization patterns are compared for four different positions in the sequence. Only the $p^{25,13}$ probes are shown. The top panel of each pair shows the hybridization of the mt3 target, which matches the chip $P^0$ sequence at these positions. The lower panel shows the pattern generated by a sample from a patient with Leber's hereditary optic neuropathy (LHON). Three known pathogenic mutations, LHON3460, LHON4216, and LHON13708, are clearly detected. For comparison, the fourth panel in the set shows a region around position 11,778 that is identical in both samples.

We therefore designed a $P^{25,13}$ tiling array for the mitochondrial genome. The array contains a total of 136,528 synthesis cells, each ~35×35 μm in size (FIG. 3). In addition to a 4L tiling across the genome, the array contains a set of probes representing a single base deletion at every position across the genome, and sets of probes designed to match a range of specific mtDNA haplotypes. Using long range PCR, the 16.6 kb mtDNA was amplified directly from genomic DNA samples. Lone range PCR amplification was carried out on genomic DNA using Perkin Elmer GeneAmp XL PCR reagents according to the manufactures's protocol. Primers were L14836-T3 (5'aattaaccctcactaaagggAT-GAAACTTCGGCTCACTCCTTGGC) (SEQ ID NO:9) and RH1066-T7 (5'taatacgactcactatagggaTTTCAT-CATGCGGAGATGTTGGATGG) (SEQ ID NO:10), based on RH 1066 [Cheng et al., *Nature Genetics* 7, 350-351 (1994)]. Each 100 μl reaction contained 0.2 μM of each primer and ~10-50 ng total genomic DNA. Transcription reactions were carried out using Ambion MAXIscript kit using the manufactures's protocol. The concentration of the 16.6 kb PCR template was ~2 nM and the reaction was spiked with 0.2 mM biotin-16-UTP. Incubation was at 37° C. for 2 h. Fragmentation and hybridization were as described above, except that 3.5 M TMAC1 and 5' biotin-CTGAACG-GTAGCATCTTGAC (SEQ ID NO:11) were used in the hybridization buffer, which also contained 100 μg/ml fragmented baker's yeast RNA (Sigma); and hybridization was carried out at 40° C. for 4 h. Labeled RNA targets were prepared by in vitro transcription and hybridized to the array. Genomic hybridization patterns were imaged in less than 10 minutes by a high resolution confocal microscope.

A custom telocentric objective lens with a numerical aperture of 0.25 focuses 5 mW of 488 nm argon laser light to a 3 μm diameter spot, which is scanned by a galvanometer mirror across a 14 mm field at 30 lines/sec. Fluorescence collected by the objective is descanned by the galvanometer mirror, filtered by a dichroic beamsplitter (555 nm) and a bandpass filter (555-607 nm), focused onto a confocal pinhole, and detected by a photomultiplier. Photomultiplier output is digitized to 12 bits. A 4096×4096 pixel image is obtained in less than 3 min. Pixel size is 3.4 μm. The data from four sequential scans were summed to improve signal to noise.

FIG. 3B shows the hybridization pattern of a 16. kb target to the mitochondrial genome chips. Although there are some regions of low intensity, most of the 25-mer array hybridized efficiently: simply by identifying the highest intensity in each column of 4 substitution probes, 99.0% of the mt3 sequence could be read correctly ($P^0$ sequence=mt3). The array was used to successfully detect three disease-causing mutations in a mitochondrial DNA sample from a patient suffering from Leber's hereditary optic neuropathy (Brown et al., *FASEB J.* 6, 2791-2799 (1992)) (FIG. 3C). Furthermore, 7 errors and undetected polymorphisms from the gel-based sequence were identified.

We then hybridized 10 African genomes to the array and unambiguously identified 505 polymorphisms. There were polymorphisms that could be clearly read and for which a confirmatory footprint was detected automatically. For the 10 samples, the 2.5 kb cytochrome b and control region sequences were known. No false positives were detected in the ~25 kb of sequence checked in this way. Additional clustered polymorphisms were detected by the presence of footprints, but not read directly.

The throughput of the system we describe is 5 chips per hour. Thus, 50 genomes can be read by hybridization in the time it takes to read 2 genomes conventionally. Furthermore, there are drastic reductions in sample preparation needs, because the entire genome is labeled in a single reaction, at a cost similar to that for a single sequencing reaction. Also, sequence reading at the level of data analysis is automated: the sequences can be read in a matter of minutes. No analytical separations or gel preparation are needed, which contributes to the speed of the experiment. Finally, a clear advantage to the approach we describe is that it is highly scalable. The cost, effort and time required to analyze the entire 16.6 kb mtDNA in a single experiment is virtually identical to that required to read 2.5 kb.

From the foregoing, it is apparent that the invention includes a number of general uses that can be expressed concisely as follows. The invention provides for the use of any of the nucleic acid segments described above in the diagnosis or monitoring of diseases, such as Alzheimer's disease, cancer, inflammation, heart disease, diseases of the CNS, and susceptibility to infection by microorganisms. The invention further provides for the use of any of the nucleic acid segments in the manufacture of a medicament for the treatment or prophylaxis of such diseases. The invention further provides for the use of any of the DNA segment as a pharmaceutical.

Although the foregoing invention has been described in detail for purposes of clarity of understanding, it will be obvious that certain modifications may be practiced within the scope of the appended claims. All publications and patent documents cited above are hereby incorporated by reference in their entirety for all purposes to the same extent as if each were so individually denoted.

TABLE I

| pos | rbase | asn_base | HA001_v_mt2 | HA002_v_mt2 | HA004_v_mt2 | HA007_v_mt2 | IB013_v_mt2 | IGF002_v_mt2 | IGF005_v_mt2 | IGF007_v_mt2 | HA001_v_mt2 | YR019 |
|---|---|---|---|---|---|---|---|---|---|---|---|---|
| 64 | C | c | C | C | T | C | C | C | C | C | C | C |
| 73 | G | a | G | G | A | G | G | G | G | G | G | G |
| 93 | A | a | A | g | G | G | A | A | A | A | A | A |
| 182 | C | c | T | T | c | T | c | t | C | C | C | C |
| 195 | T | t | c | C | t | C | t | c | T | C | C | C |
| 235 | G | a | A | A | g | A | a | A | A | A | A | A |
| 247 | G | g | G | G | A | G | a | G | G | G | G | G |
| 297 | A | a | A | A | A | A | G | A | A | A | A | A |
| 316 | G | g | G | G | G | G | A | G | G | G | G | G |
| 325 | C | c | C | T | C | T | C | C | C | C | C | C |
| 663 | G | a | A | A | A | A | A | A | A | A | A | A |
| 680 | T | t | T | C | T | C | T | T | T | T | T | T |
| 709 | G | g | A | A | G | A | G | A | G | G | G | G |
| 769 | G | g | A | a | a | a | a | A | G | A | A | a |
| 825 | T | t | T | T | A | T | A | T | T | T | T | T |
| 1018 | G | g | A | A | A | A | A | A | G | A | A | A |
| 1040 | T | t | T | T | T | C | T | T | T | T | T | T |
| 1048 | C | c | C | C | T | C | C | C | C | C | C | C |
| 1442 | G | g | A | A | G | A | G | A | G | G | G | G |
| 1706 | C | c | T | C | C | C | C | T | C | C | C | C |
| 1736 | G | a | A | A | A | A | A | A | A | A | A | A |
| 2358 | A | a | G | A | A | A | A | G | A | A | A | A |
| 2416 | T | t | t | t | T | t | T | A | T | n | t | t |
| 2758 | G | g | G | G | A | G | A | G | G | G | G | G |
| 2789 | C | c | C | C | C | C | C | C | C | T | T | T |
| 2885 | T | t | T | T | C | T | C | T | T | T | T | T |
| 3010 | G | g | G | G | G | G | G | G | G | G | G | A |
| 3200 | T | t | T | A | T | A | T | T | T | T | T | T |
| 3336 | T | t | T | T | T | T | T | T | T | T | C | T |
| 3337 | G | g | G | A | G | G | G | G | G | G | G | G |
| 3450 | C | c | C | C | C | C | C | C | T | C | C | C |
| 3516 | C | c | C | C | A | C | C | C | C | C | C | C |
| 3594 | C | c | T | T | T | t | c | T | C | T | T | T |
| 3648 | C | c | T | C | C | C | C | C | C | C | C | C |
| 3666 | G | g | G | G | G | G | A | G | G | G | G | G |
| 3745 | G | g | G | A | G | G | G | G | G | G | G | G |
| 3866 | T | t | T | T | C | T | T | T | T | T | T | T |
| 3918 | G | g | G | G | G | G | G | G | G | A | A | G |
| 4104 | A | a | G | G | G | G | G | G | A | G | G | G |
| 4158 | A | a | G | A | A | A | A | G | A | A | A | A |
| 4248 | C | t | T | T | T | T | T | T | T | T | T | T |
| 4312 | C | c | C | C | T | C | C | C | C | C | C | C |
| 4586 | T | t | T | T | C | T | T | T | T | T | T | T |
| 4767 | A | a | G | A | A | A | A | G | A | A | A | A |
| 4824 | G | a | A | A | A | A | A | A | A | A | A | A |
| 4967 | T | t | T | T | T | C | T | T | T | T | T | T |
| 5027 | C | c | T | C | C | C | C | T | C | C | C | C |
| 5096 | T | t | T | T | C | T | T | T | T | T | T | T |
| 5147 | G | g | G | G | G | G | G | G | G | G | A | G |
| 5231 | G | g | G | G | A | G | G | G | G | G | G | G |
| 5252 | G | g | G | G | G | G | G | G | G | G | G | A |
| 5285 | A | a | A | A | A | A | A | A | A | g | G | A |
| 5331 | C | c | A | C | C | C | C | A | C | C | C | C |
| 5460 | G | g | G | G | A | G | G | G | G | G | G | G |
| 5603 | C | c | C | C | T | C | C | C | C | C | C | C |
| 5773 | G | g | G | G | G | G | G | G | A | G | G | G |

TABLE I-continued

| pos | rbase | asn_base | HA001_v_mt2 | HA002_v_mt2 | HA004_v_mt2 | HA007_v_mt2 | IB013_v_mt2 | IGF002_v_mt2 | IGF005_v_mt2 | IGF007_v_mt2 | HA001_v_mt2 | YR019 |
|---|---|---|---|---|---|---|---|---|---|---|---|---|
| 5814 | T | t | C | T | T | T | T | C | T | T | T | T |
| 5823 | A | a | A | A | A | G | A | A | A | A | A | A |
| 5912 | C | c | T | C | C | C | C | C | C | C | C | C |
| 6071 | T | t | T | T | T | T | C | T | T | T | T | T |
| 6150 | G | g | G | G | G | G | A | G | G | G | G | G |
| 6237 | C | c | C | C | C | C | C | C | T | C | C | C |
| 6253 | T | t | T | T | T | T | C | T | T | T | T | T |
| 6527 | G | a | A | A | A | A | A | A | A | A | A | A |
| 6614 | T | t | C | T | T | T | T | C | T | T | T | T |
| 6663 | A | a | A | A | A | A | A | A | A | A | A | G |
| 6713 | C | c | T | C | C | C | C | T | C | C | C | C |
| 6806 | A | a | C | A | A | A | A | G | A | A | A | A |
| 6827 | T | t | T | C | T | T | T | T | T | T | T | T |
| 6875 | C | c | C | C | C | C | C | C | C | A | C | C |
| 7146 | A | a | A | A | G | A | G | A | A | A | A | A |
| 7175 | T | t | T | T | T | T | T | T | T | C | C | C |
| 7256 | C | c | T | T | T | T | T | T | T | C | T | T |
| 7274 | C | c | C | C | C | C | C | C | C | T | T | T |
| 7389 | T | t | T | T | T | T | C | T | T | T | T | T |
| 7518 | A | a | A | n | A | G | a | a | A | N | A | A |
| 7521 | G | g | A | c | A | G | g | g | G | A | A | A |
| 7624 | T | t | A | A | T | A | T | A | T | T | T | T |
| 7771 | A | a | A | A | A | A | A | A | A | G | G | g |
| 8027 | A | g | G | G | G | G | A | G | G | G | G | G |
| 8080 | C | c | T | C | C | C | C | T | C | C | C | C |
| 8206 | G | g | A | A | G | A | G | A | G | A | A | A |
| 8387 | G | g | A | G | G | G | G | A | G | G | G | G |
| 8428 | C | c | C | C | T | C | C | C | C | C | C | C |
| 8468 | C | c | c | C | T | C | T | C | C | C | c | C |
| 8503 | T | t | C | T | T | c | T | C | T | T | T | T |
| 8566 | A | a | A | A | G | A | A | A | A | A | A | A |
| 8655 | C | c | C | C | T | C | T | C | C | C | C | C |
| 8701 | A | a | G | G | G | G | G | G | G | G | G | G |
| 8784 | A | a | A | A | A | A | G | A | A | A | A | A |
| 8794 | T | c | C | C | C | C | C | C | C | C | C | C |
| 8854 | G | g | G | G | G | G | G | G | G | G | G | A |
| 8877 | T | t | T | T | T | T | C | T | T | T | T | T |
| 9042 | C | c | C | C | T | C | C | C | C | C | C | C |
| 9072 | A | a | A | A | A | A | C | A | A | A | A | A |
| 9221 | A | a | G | G | A | G | A | G | A | G | G | G |
| 9347 | A | a | A | A | G | A | A | A | A | A | A | A |
| 9449 | C | c | C | C | C | C | C | C | T | C | C | C |
| 9818 | C | c | C | C | T | C | C | C | C | C | C | C |
| 10031 | T | t | T | T | T | T | C | T | T | T | T | T |
| 10115 | T | t | C | C | T | c | T | C | T | C | C | T |
| 10321 | T | t | T | T | T | T | C | T | T | T | T | T |
| 10373 | G | g | G | G | G | G | G | A | G | G | G | G |
| 10586 | C | g | G | G | g | G | A | G | G | G | G | G |
| 10664 | C | c | C | C | T | C | C | C | C | C | C | C |
| 10688 | G | g | G | G | A | G | A | G | G | G | G | G |
| 10793 | C | c | C | C | C | C | T | C | C | C | C | C |
| 10810 | T | t | T | T | C | T | C | T | T | T | T | T |
| 10828 | T | t | T | T | T | T | C | T | T | T | T | T |
| 10873 | T | t | C | C | C | C | C | C | C | C | C | C |
| 10915 | T | t | T | T | C | T | T | T | T | T | t | T |
| 11164 | A | a | A | A | A | A | G | A | A | A | A | A |
| 11176 | A | g | G | G | A | G | G | G | G | G | G | G |
| 11641 | A | a | A | A | G | A | A | A | A | A | A | A |
| 11654 | A | a | A | A | A | A | G | A | A | A | A | A |
| 11800 | A | a | A | A | A | A | A | A | G | A | A | A |
| 11914 | G | g | G | G | A | G | G | G | G | A | A | A |
| 11944 | T | t | C | C | T | C | T | C | T | C | C | C |
| 12007 | A | g | G | G | A | G | G | G | G | G | G | G |
| 12049 | C | c | C | C | C | C | T | C | C | C | C | C |
| 12115 | C | c | C | C | C | C | T | C | C | C | C | C |
| 12236 | G | g | A | A | G | A | G | A | G | G | G | G |
| 12354 | T | t | T | T | T | T | T | T | T | T | T | C |
| 12477 | T | t | T | T | T | T | C | T | T | T | T | T |
| 12720 | A | a | A | A | G | A | A | A | A | A | A | A |
| 12777 | A | a | G | A | A | A | A | A | A | A | A | A |
| 12810 | A | a | A | A | A | A | G | A | A | A | A | A |
| 12948 | A | a | A | A | A | A | G | A | A | A | A | A |
| 13105 | A | a | A | A | G | A | G | A | G | A | A | A |
| 13149 | A | a | A | A | A | A | G | A | A | A | A | A |
| 13184 | T | t | T | T | T | C | T | T | T | T | T | T |
| 13203 | A | a | A | A | A | G | A | A | A | A | A | A |

TABLE I-continued

| pos | rbase | asn_base | HA001_v_mt2 | HA002_v_mt2 | HA004_v_mt2 | HA007_v_mt2 | IB013_v_mt2 | IGF002_v_mt2 | IGF005_v_mt2 | IGF007_v_mt2 | HA001_v_mt2 | YR019 |
|---|---|---|---|---|---|---|---|---|---|---|---|---|
| 13276 | A | a | A | A | G | A | A | A | A | A | A | A |
| 13485 | A | a | A | A | A | A | G | A | A | A | A | A |
| 13506 | C | c | C | C | T | C | t | C | C | C | C | C |
| 13590 | G | g | a | A | G | A | G | A | G | A | A | A |
| 13650 | C | c | t | t | t | t | T | T | C | T | T | t |
| 13789 | T | t | T | T | T | T | C | T | T | T | t | T |
| 13803 | A | a | A | A | A | A | A | A | A | g | G | g |
| 13914 | C | c | C | C | C | C | C | C | A | C | C | C |
| 13958 | G | g | G | C | G | C | G | G | G | G | G | G |
| 13966 | A | a | G | A | A | A | A | G | A | A | A | A |
| 14000 | T | t | T | T | T | T | A | T | T | T | T | T |
| 14059 | A | a | G | A | A | A | A | G | A | A | A | A |
| 14178 | T | t | T | T | T | T | C | T | T | T | T | T |
| 14308 | T | t | T | T | C | T | T | T | T | T | T | T |
| 14407 | C | c | T | C | C | C | C | T | C | C | C | C |
| 14560 | C | g | G | G | G | G | A | G | G | G | G | G |
| 14566 | A | a | A | A | A | A | A | A | A | G | G | G |
| 14911 | C | c | C | C | C | C | T | C | C | C | C | C |
| 15043 | G | g | G | G | G | A | G | G | G | G | G | G |
| 15067 | T | t | T | T | T | T | C | T | T | T | T | T |
| 15110 | G | g | A | A | G | A | G | A | G | G | G | G |
| 15119 | G | g | G | G | G | G | G | G | G | G | G | A |
| 15136 | C | c | C | C | T | C | C | C | C | C | C | C |
| 15217 | G | g | A | A | G | A | G | A | G | G | G | G |
| 15244 | A | a | A | A | A | A | A | A | A | G | G | A |
| 15301 | G | g | A | A | G | A | G | A | a | A | A | A |
| 15431 | G | g | G | G | A | G | G | G | G | G | G | G |
| 15629 | T | t | T | T | T | T | T | T | T | C | C | T |
| 15734 | G | g | G | G | G | G | G | G | G | G | G | A |
| 15784 | T | t | T | T | T | T | T | T | T | C | C | C |

What is claimed is:

1. An isolated segment of human mitochondrial DNA or RNA of between 10 and 100 bases including a polymorphic site shown in Table 1 selected from the group consisting of 235, 297, 325, 680, 1040, 1442, 1706, 2358, 2416, 2789, 3337, 3450, 3516, 3594, 3648, 3666, 3745, 3866, 3918, 4104, 4158, 4586, 4767, 4967, 5027, 5096, 5252, 5285, 5773, 5814, 5823, 6071, 6150, 6237, 6253, 6527, 6614, 6663, 6713, 6806, 6827, 6875, 7146, 7389, 7518, 7624, 8080, 8387, 8503, 8566, 8655, 8854, 8877, 9042, 9072, 9347, 9449, 9818, 10031, 10321, 10664, 10688, 10793, 10810, 10828, 11164, 11176, 11641, 11800, 12049, 12115, 12354, 12477, 12777, 12948, 13149, 13184, 13276, 13485, 13506, 13914, 14000, 14059, 14407, 15119, 15136, 15431, 15629, 15734, 15849, 15883, 15902, 16093, 16114, 16124, 16126, 16264, 16290, 16318, 16319, 16354, and 16390, or the perfect complement of the full length of the segment.

2. The segment of claim 1, wherein the polymorphic form occupying the polymorphic site is an alternative form listed in Table 1, column 2, or 4-11, wherein the alternate form is other than the base listed in Table 1, column 3 for the polymorphic site.

3. The segment of claim 1, wherein the polymorphic site is at a position selected from the group consisting of 235, 297, and 325.

4. The segment of claim 1, wherein the polymorphic site is at a position selected from the group consisting of 680, 1040, 1442, and 1706.

5. The segment of claim 1, wherein the polymorphic site is at a position selected from the group consisting of 2358, 2416, 2789, and 3337.

6. The segment of claim 1, wherein the polymorphic site is at a position selected from the group consisting of 3450, 3516, 3594, 3648, 3666, 3745, 3866, 3918, 4104, and 4158.

7. The segment of claim 1, wherein the polymorphic site is at a position selected from the group consisting of 4586, 4767, 4967, 5027, and 5096.

8. The segment of claim 1, wherein the polymorphic site is at a position selected from the group consisting of 5252, 5285, 5773, 5814, 5823, and 6071.

9. The segment of claim 1, wherein the polymorphic site is at a position selected from the group consisting of 6150, 6237, 6253, 6527, 6614, 6663, 6713, 6806, 6827 and 6875.

10. The segment of claim 1, wherein the polymorphic site is at a position selected from the group consisting of 7146, 7175, 7256, 7274, 7389, 7518, and 7624.

11. The segment of claim 1, wherein the polymorphic site is at a position selected from the group consisting of 8387, 8503, 8566, 8655, and 8784.

12. The segment of claim 1, wherein the polymorphic site is at a position selected from the group consisting of 8854, 8877, 9042, 9072, 9221, 9347, 9449, 9818 and 10031.

13. The segment of claim 1, wherein the polymorphic site is at a position selected from the group consisting of 10115, 10321, 10373, 10664, 10688, 10793, 10810, and 10828.

14. The segment of claim 1, wherein the polymorphic sits is at a position selected from the group consisting of 11164, 11176, 11641, 11800, and 12049.

15. The segment of claim 1, wherein the polymorphic site is at a position selected from the group consisting of 12115, 12354, 12477, 12720, 12777, 12948, and 13149.

16. The segment of claim 1, wherein the polymorphic site is at a position selected from the group consisting of 13184, 13203, 13276, 13485, 13506, 13650, 13789, 13803 and 13914.

17. The segment of claim 1, wherein the polymorphic site is at a position selected from the group consisting of 13966, 14000, 14059, 14178, 14308, 14407, 14566 and 14911.

18. The segment of claim 1, wherein the polymorphic site is at a position selected from the group consisting of 15119, 15136, 15244, 15431 and 15629.

19. The segment of claim 1, wherein the polymorphic site is at a position selected from the group consisting of 15734, 15784, 15849, 15883, 15902, 16114, 16124 and 16126.

20. The segment of claim 1, wherein the polymorphic site is at a position selected from the group consisting of 16264, 16318, and 16354.

21. An allele-specific oligonucleotide that is perfectly complementary to a segment of human mitochondrial nucleic acid or its perfect complement including a polymorphic site selected from the group consisting of 235, 297, 325, 680, 1040, 1442, 1706, 2358, 2416, 2789, 3337, 3450, 3516, 3594, 3648, 3666, 3745, 3866, 3918, 4104, 4158, 4586, 4767, 4967, 5027, 5096, 5252, 5285, 5773, 5814, 5823, 6071, 6150, 6237, 6253, 6527, 6614, 6663, 6713, 6806, 6827, 6875, 7146, 7389, 7518, 7624, 8080, 8387, 8503, 8566, 8655, 8854, 8877, 9042, 9072, 9347, 9449, 9818, 10031, 10321, 10664, 10688, 10793, 10810, 10828, 11164, 11176, 11641, 11800, 12049, 12115, 12354, 12477, 12777, 12948, 13149, 13184, 13276, 13485, 13506, 13914, 14000, 14059, 14407, 15119, 15136, 15431, 15629, 15734, 15849, 15883, 15902, 16093, 16114, 16124, 16126, 16264, 16290, 16318, 16319, 16354, and 16390, or the perfect complement of the full length of the segment.

22. The allele-specific oligonucleotide of claim 21 that is a probe.

23. The allele-specific oligonucleotide of claim 21, wherein a central position of the probes aligns with the polymorphic site of the fragment.

24. The allele-specific oligonucleotide of claim 21 that is a primer.

25. The allele-specific oligonucleotide of claim 24, wherein the 3' end of the primer aligns with the polymorphic site of the fragment.

26. An isolated nucleic acid comprising a segment of at least 10 contiguous bases from SEQ ID NO:30, or the perfect complement of the full length thereof, including a polymorphic site shown in Table 1 selected from the group consisting of 235, 247, 297, 325, 680, 1040, 1442, 1706, 2358, 2416, 2789, 3200, 3337, 3450, 3516, 3594, 3648, 3666, 3745, 3866, 3918, 4104, 4158, 4586, 4767, 4967, 5027, 5096, 5252, 5285, 5331, 5773, 5814, 5823, 5912, 6071, 6150, 6237, 6253, 6527, 6614, 6663, 6713, 6806, 6827, 6875, 7146, 7389, 7518, 7624, 8080, 8387, 8503, 8566, 8655, 8854, 8877, 9042, 9072, 9347, 9449, 9818, 10031, 10321, 10664, 10688, 10793, 10810, 10828, 11164, 11176, 11641, 11800, 12049, 12115, 12354, 12477, 12777, 12948, 13149, 13184, 13276, 13485, 13506, 13914, 14000, 14059, 14407, 15119, 15136, 15431, 15629, 15734, 15849, 15883, 15902, 16093, 16114, 16124, 16126, 16264, 16290, 16318, 16319, 16354, and 16390, wherein the polymorphic site within the segment is occupied by a base other than the base shown in Table 1, column 3 ("asn base").

27. The isolated nucleic acid of claim 26, wherein the polymorphic site is at a position selected from the group consisting of 235, 297, and 325.

28. The isolated nucleic acid of claim 26, the polymorphic site is at a position selected from the group consisting of 680, 1040, 1442, and 1706.

29. The isolated nucleic acid of claim 26, wherein the polymorphic site is at a position selected from the group consisting of 2358, 2416, 2789, 3200, and 3337.

30. The isolated nucleic acid of claim 26, wherein the polymorphic site is at a position selected from the group consisting of 3450, 3516, 3594, 3648, 3666, 3745, 3866, 3918, 4104, and 4158.

31. The isolated nucleic acid of claim 26, wherein the polymorphic site is at a position selected from the group consisting of 4586, 4767, 4967, 5027, and 5096.

32. The isolated nucleic acid of claim 26, wherein the polymorphic site is at a position selected from the group consisting of 5252, 5285, 5331, 5773, 5814, 5823, 5912, and 6071.

33. The isolated nucleic acid of claim 26, wherein the polymorphic site is at a position selected from the group consisting of 6150, 6237, 6253, 6527, 6614, 6663, 6713, 6806, 6827 and 6875.

34. The isolated nucleic acid of claim 26, wherein the polymorphic site is at a position selected from the group consisting of 6150, 6253 and 6663.

35. The isolated nucleic acid of claim 26, wherein the polymorphic site is at a position selected from the group consisting of 7146, 7175, 7256, 7274, 7389, 7518, and 7624.

36. The isolated nucleic acid of claim 26, wherein the polymorphic site is at a position selected from the group consisting of 8387, 8503, 8566, 8655, and 8784.

37. The isolated nucleic acid of claim 26, wherein the polymorphic site is at a position selected from the group consisting of 8854, 8877, 9042, 9072, 9221, 9347, 9449, 9818 and 10031.

38. The isolated nucleic acid of claim 26, wherein the polymorphic site is at a position selected from the group consisting of 10115, 10321, 10373, 10664, 10688, 10793, 10810, and 10828.

39. The isolated nucleic acid of claim 26, wherein the polymorphic site is at a position selected from the group consisting of 11164, 11176, 11641, 11800, and 12049.

40. The isolated nucleic acid of claim 26, wherein the polymorphic site is at a position selected from the group consisting of 12115, 12354, 12477, 12720, 12777, 12948, and 13149.

41. The isolated nucleic acid of claim 26, wherein the polymorphic site is at a position selected from the group consisting of 13184, 13203, 13276, 13485, 13506, 13650, 13789, 13803 and 13914.

42. The isolated nucleic acid of claim 26, wherein the polymorphic site is at a position selected from the group consisting of 13966, 14000, 14059, 14178, 14308, 14407, 14566 and 14911.

43. The isolated nucleic acid of claim 26, wherein the polymorphic site is at a position selected from the group consisting of 15119, 15136, 15244, 15431 and 15629.

44. The isolated nucleic acid of claim 26, wherein the polymorphic site is at a position selected from the group consisting of 15734, 15784, 15849, 15883, 15902, 16114, 16124 and 16126.

45. The isolated nucleic acid of claim 26, wherein the polymorphic site is at a position selected from the group consisting of 16264, 16318, and 16354.

46. A method of analyzing a nucleic acid comprising:
obtaining the nucleic acid from an individual; and
identifying a base occupying a polymorphic site shown in Table 1 selected from the group consisting of 235, 247, 297, 325, 680, 1040, 1442, 1706, 2358, 2416, 2789, 3200, 3337, 3450, 3516, 3594, 3648, 3666, 3745, 3866, 3918, 4104, 4158, 4586, 4767, 4967, 5027, 5096, 5252, 5285, 5331, 5773, 5814, 5823, 5912, 6071, 6150, 6237, 6253, 6527, 6614, 6663, 6713, 6806, 6827, 6875, 7146, 7389, 7518, 7624, 8080, 8387, 8503, 8566, 8655, 8854, 8877, 9042, 9072, 9347, 9449, 9818, 10031, 10321, 10664, 10688, 10793, 10810, 10828, 11164, 11176, 11641, 11800, 12049, 12115, 12354, 12477, 12777, 12948, 13149, 13184, 13276, 13485, 13506, 13914, 14000, 14059, 14407, 15119, 15136, 15431, 15629, 15734, 15849, 15883, 15902, 16093, 16114, 16124, 16126, 16264, 16290, 16318, 16319, 16354, and 16390, wherein the base is a base other than the base shown in Table 1, column 3 ("asn base").

47. The method of claim 46, wherein the polymorphic site is at a position selected from the group consisting of 235, 297, and 325.

48. The method of claim 46, wherein the polymorphic site is at a position selected from the group consisting of 680, 1040, 1442, and 1706.

49. The method of claim 46, wherein the polymorphic site is at a position selected from the group consisting of 2358, 2416, 2789, 3200, and 3337.

50. The method of claim 46, wherein the polymorphic site is at a position selected from the group consisting of 3450, 3516, 3594, 3648, 3666, 3745, 3866, 3918, 4104, and 4158.

51. The method of claim 46, wherein the polymorphic site is at a position selected from the group consisting of 4586, 4767, 4967, 5027, and 5096.

52. The method of claim 46, wherein the polymorphic site is at a position selected from the group consisting of 5252, 5285, 5331, 5773, 5814, 5823, 5912, and 6071.

53. The method of claim 46, wherein the polymorphic site is at a position selected from the group consisting of 6150, 6237, 6253, 6527, 6614, 6663, 6713, 6806, 6827 and 6875.

54. The method of claim 46, wherein the polymorphic site is at a position selected from the group consisting of 6150, 6253 and 6663.

55. The method of claim 46, wherein the polymorphic site is at a position selected from the group consisting of 7146, 7175, 7256, 7274, 7389, 7518, and 7624.

56. The method of claim 46, wherein the polymorphic site is at a position selected from the group consisting of 8387, 8503, 8566, 8655, and 8784.

57. The method of claim 46, wherein the polymorphic site is at a position selected from the group consisting of 8854, 8877, 9042, 9072, 9221, 9347, 9449, 9818 and 10031.

58. The method of claim 46, wherein the polymorphic site is at a position selected from the group consisting of 10115, 10321, 10373, 10664, 10688, 10793, 10810, and 10828.4.

59. The method of claim 46, wherein 1, wherein the polymorphic site is at a position selected from the group consisting of 11164, 11176, 11641, 11800, and 12049.

60. The method of claim 46, wherein the polymorphic site is at a position selected from the group consisting of 12115, 12354, 12477, 12720, 12777, 12948, and 13149.

61. The method of claim 46, wherein the polymorphic site is at a position selected from the group consisting of 13184, 13203, 13276, 13485, 13506, 13650, 13789, 13803 and 13914.

62. The method of claim 46, wherein the polymorphic site is at a position selected from the group consisting of 13966, 14000, 14059, 14178, 14308, 14407, 14566 and 14911.

63. The method of claim 46, wherein the polymorphic site is at a position selected from the group consisting of 15119, 15136, 15244, 15431 and 15629.

64. The method of claim 46, wherein the polymorphic site is at a position selected from the group consisting of 15734, 15784, 15849, 15883, 15902, 16114, 16124 and 16126.

65. The method of claim 46, wherein the polymorphic site is at a position selected from the group consisting of 16264, 16318, and 16354.

* * * * *